US012760093B2

(12) United States Patent
Zhou et al.

(10) Patent No.: US 12,760,093 B2
(45) Date of Patent: Oct. 13, 2026

(54) CLDN18.2 ANTIBODY AND USE THEREOF

(71) Applicant: Shanghai Escugen Biotechnology Co., Ltd., Shanghai (CN)

(72) Inventors: Qing Zhou, Shanghai (CN); Chuanying Xu, Shanghai (CN); Weihong Nian, Shanghai (CN); Xiangyu He, Shanghai (CN); Xinmin Zhang, Shanghai (CN); Xintong Zheng, Shanghai (CN); Feng He, Shanghai (CN); Jing Xiao, Shanghai (CN)

(73) Assignee: Shanghai Escugen Biotechnology Co., Ltd., Shanghai (CN)

( * ) Notice: Subject to any disclaimer, the term of this patent is extended or adjusted under 35 U.S.C. 154(b) by 1032 days.

(21) Appl. No.: 17/798,863

(22) PCT Filed: Feb. 10, 2021

(86) PCT No.: PCT/CN2021/076481
§ 371 (c)(1),
(2) Date: Aug. 10, 2022

(87) PCT Pub. No.: WO2021/160154
PCT Pub. Date: Aug. 19, 2021

(65) Prior Publication Data

US 2023/0312704 A1 Oct. 5, 2023

(30) Foreign Application Priority Data

Feb. 10, 2020 (CN) ......................... 202010084476.3

(51) Int. Cl.
*C07K 16/28* (2006.01)
*A61P 35/00* (2006.01)
*C12N 15/63* (2006.01)

(52) U.S. Cl.
CPC .............. *C07K 16/28* (2013.01); *A61P 35/00* (2018.01); *C12N 15/63* (2013.01); *C07K 2317/24* (2013.01); *C07K 2317/31* (2013.01); *C07K 2317/565* (2013.01)

(58) Field of Classification Search
CPC ................ C07K 16/28; C07K 2317/24; C07K 2317/31; C07K 2317/565; A61P 35/00; G01N 33/57492; G01N 33/574; A61K 2039/505
See application file for complete search history.

(56) References Cited

U.S. PATENT DOCUMENTS

| | | | |
|---|---|---|---|
| 9,512,232 | B2 | 12/2016 | Sahin et al. |
| 9,770,487 | B2 | 9/2017 | Sahin et al. |
| 2015/0374789 | A1 | 12/2015 | Sahin et al. |
| 2018/0000900 | A1 | 1/2018 | Sahin et al. |
| 2018/0319891 | A1 | 11/2018 | Sahin et al. |
| 2019/0233511 | A1 | 8/2019 | Wang et al. |
| 2019/0298803 | A1 | 10/2019 | Sahin et al. |
| 2020/0040101 | A1 | 2/2020 | Lu et al. |
| 2020/0385463 | A1 | 12/2020 | Li |
| 2020/0399364 | A1 | 12/2020 | Wang et al. |
| 2021/0023177 | A1 | 1/2021 | Sahin et al. |
| 2023/0312704 | A1 | 10/2023 | Zhou et al. |

FOREIGN PATENT DOCUMENTS

| | | | | |
|---|---|---|---|---|
| CA | 3167349 A1 | 8/2021 | | |
| CN | 104321345 B | 3/2018 | | |
| CN | 110606891 A | 12/2019 | | |
| CN | 109790222 B | 3/2022 | | |
| CN | 119264213 A | 1/2025 | | |
| EP | 3483182 A1 | 5/2019 | | |
| EP | 3808376 A1 | 4/2021 | | |
| WO | WO 2013167259 A1 | 11/2013 | | |
| WO | WO 2014127785 A1 | 8/2014 | | |
| WO | WO 2019/174617 A1 | 9/2019 | | |
| WO | WO 2019173420 A1 | 9/2019 | | |
| WO | WO-2019219089 A1 | * | 11/2019 | ......... G01N 33/5758 |
| WO | WO 2019/242505 A1 | 12/2019 | | |
| WO | WO 2020018852 A2 | 1/2020 | | |

OTHER PUBLICATIONS

Paul, WE, "Fundamental Immunology: Third Edition", 1993, Raven Press, 292-295. (Year: 1993).*
Bendig, MM, "Humanization of Rodent Monoclonal Antibodies by CDR Grafting", 1995, Methods: A Companion to Methods in Enzymology, 8, 83-93. (Year: 1995).*
Baxevanis, CN, "Antibody-based cancer therapy", 2008, Expert Opin. Drug Discov., 3(4), 441-452. (Year: 2008).*
Dottermusch, M. et al. "Expression of the Potential Therapeutic Target Claudin-18.2 is Frequently Decreased in Gastric Cancer: Results from a Large Caucasian Cohort Study." Virchows Archiv, vol. 475, Jul. 22, 2019, pp. 563-571.
European Patent Office, Extended European Search Report, European Patent Application No. 21753717.4, Feb. 23, 2024, 12 pages.
European Patent Office, Extended European Search Report, European Patent Application No. 21754619.1, Feb. 23, 2024, 11 pages.
PCT International Search Report, PCT Application No. PCT/CN2021/076482, Apr. 28, 2021, six pages.
Singh, P. et al. "Anti-Claudin 18.2 Antibody as New Targeted Therapy for Advanced Gastric Cancer." Journal of Hematology & Oncology, vol. 10, No. 105, May 12, 2017, pp. 1-5.
U.S. Appl. No. 10/314,890 B2, filed Jun. 11, 2019, Ganymed Pharmaceuticals AG, et al.
PCT International Search Report (with English translation), PCT/CN2021/076481, May 12, 2021, 9 Pages.

(Continued)

*Primary Examiner* — Laura B Goddard
*Assistant Examiner* — Alyssa Rae Stonebraker
(74) *Attorney, Agent, or Firm* — Fenwick & West LLP

(57) ABSTRACT

Provided are an antibody against claudin 18.2 (CLDN18.2) and a use thereof in diagnosing and treating cancer of the stomach, pancreas and esophagus.

19 Claims, 11 Drawing Sheets

Specification includes a Sequence Listing.

(56) References Cited

OTHER PUBLICATIONS

Chen, Siyuan, et al., "Advances in the Application of Claudins to Tumor Therapy," Chinese Journal of Biotechnology, Jun. 25, 2019, vol. 35, No. 6, pp. 931-941.
Sahin, U., et al., "Claudin-18 Splice Variant 2 is a Pan-Cancer Target Suitable for Therapeutic Antibody Development," Clinical Cancer Research, Dec. 1, 2008, vol. 14, No. 23, pp. 7624-7634.
Türeci, Ö., et al., "Characterization of Zolbetuximab in Pancreatic Cancer Models," Oncoimmunology, Nov. 10, 2018, vol. 8, No. 1, Document No. e1523096, pp. 1-10.
Xu, Liange, et al., "Advances of CLDN18.2 Protein in the Therapy of Malignant Tumors," Chinese Journal of Clinical Oncology, Mar. 30, 2019, vol. 46, No. 6, pp. 311-315.
European Patent Office, Examination Report, European Patent Application No. 21753717.4, Oct. 29, 2025, 10 pages.
United States Office Action, U.S. Appl. No. 17/798,873, filed May 21, 2025, nine pages.
United States Office Action, U.S. Appl. No. 17/798,873, filed Feb. 17, 2026, nine pages.

* cited by examiner

SEQUENCE LISTING

<160> NUMBER OF SEQ ID NOS: 55

<210> SEQ ID NO 1
<211> LENGTH: 786
<212> TYPE: DNA
<213> ORGANISM: Artificial Sequence
<220> FEATURE:
<223> OTHER INFORMATION: Synthetic Sequence

<400> SEQUENCE: 1

```
atggccgtga ctgcctgtca gggcttgggg ttcgtggttt cactgattgg gattgcgggc     60

atcattgctg ccacctgcat ggaccagtgg agcacccaag acttgtacaa caaccccgta    120

acagctgttt tcaactacca ggggctgtgg cgctcctgtg tccgagagag ctctggcttc    180

accgagtgcc ggggctactt caccctgctg gggctgccag ccatgctgca ggcagtgcga    240

gccctgatga tcgtaggcat cgtcctgggt gccattggcc tcctggtatc catctttgcc    300

ctgaaatgca tccgcattgg cagcatggag gactctgcca aagccaacat gacactgacc    360

tccgggatca tgttcattgt ctcaggtctt tgtgcaattg ctggagtgtc tgtgtttgcc    420

aacatgctgg tgactaactt ctggatgtcc acagctaaca tgtacaccgg catgggtggg    480

atggtgcaga ctgttcagac caggtacaca tttggtgcgg ctctgttcgt gggctgggtc    540

gctggaggcc tcacactaat tgggggtgtg atgatgtgca tcgcctgccg gggcctggca    600

ccagaagaaa ccaactacaa agccgtttct tatcatgcct caggccacag tgttgcctac    660

aagcctggag gcttcaaggc cagcactggc tttgggtcca acaccaaaaa caagaagata    720

tacgatggag gtgcccgcac agaggacgag gtacaatctt atccttccaa gcacgactat    780

gtgtaa                                                                786
```

<210> SEQ ID NO 2
<211> LENGTH: 43
<212> TYPE: PRT
<213> ORGANISM: Artificial Sequence
<220> FEATURE:
<223> OTHER INFORMATION: Synthetic Sequence

<400> SEQUENCE: 2

```
Thr Gln Asp Leu Tyr Asn Asn Pro Val Thr Ala Val Phe Asn Tyr Gln
1               5                   10                  15

Gly Leu Trp Arg Ser Cys Val Arg Glu Ser Ser Gly Phe Thr Glu Cys
            20                  25                  30

Arg Gly Tyr Phe Thr Leu Leu Gly Leu Pro Ala
        35                  40
```

<210> SEQ ID NO 3
<211> LENGTH: 218
<212> TYPE: PRT
<213> ORGANISM: Artificial Sequence
<220> FEATURE:
<223> OTHER INFORMATION: Synthetic Sequence

<400> SEQUENCE: 3

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Val Leu Cys Trp Gly Glu
```

-continued

```
    50                  55                  60

Leu Met Asn Leu Ala Thr Trp Val Gly Ser Asn Leu Glu Asp Gly Gly
65                  70                  75                  80

Gly Gly Ser Gly Gly Gly Gly Thr Gln Asp Leu Tyr Asn Asn Pro Val
                85                  90                  95

Thr Ala Val Phe Asn Tyr Gln Gly Leu Trp Arg Ser Cys Val Arg Glu
            100                 105                 110

Ser Ser Gly Phe Thr Glu Cys Arg Gly Tyr Phe Thr Leu Leu Gly Leu
        115                 120                 125

Pro Ala Gly Gly Gly Gly Ser Gly Gly Gly Gly Ser Arg Glu Leu Val
    130                 135                 140

Val Ser Tyr Val Asn Ile Asn Met Gly Leu Lys Ile Arg Gln Leu Leu
145                 150                 155                 160

Trp Phe His Ile Ser Cys Leu Thr Phe Gly Arg Glu Thr Val Leu Glu
                165                 170                 175

Tyr Leu Val Ser Phe Gly Val Trp Ile Arg Thr Pro Pro Ala Tyr Arg
            180                 185                 190

Pro Pro Asn Ala Pro Ile Leu Ser Thr Leu Pro Glu Thr Thr Val Val
        195                 200                 205

Arg Gly Gly Ser His His His His His His
    210                 215


<210> SEQ ID NO 4
<211> LENGTH: 786
<212> TYPE: DNA
<213> ORGANISM: Artificial Sequence
<220> FEATURE:
<223> OTHER INFORMATION: Synthetic Sequence

<400> SEQUENCE: 4

atggccgtga ctgcctgtca gggcttgggg ttcgtggttt cactgattgg gattgcgggc      60

atcattgctg ccacctgcat ggaccagtgg agcacccaag acttgtacaa caaccccgta     120

acagctgttt tcaactacca ggggctgtgg cgctcctgtg tccgagagag ctctggcttc     180

accgagtgcc ggggctactt caccctgctg gggctgccag ccatgctgca ggcagtgcga     240

gccctgatga tcgtaggcat cgtcctgggt gccattggcc tcctggtatc catctttgcc     300

ctgaaatgca tccgcattgg cagcatggag gactctgcca aagccaacat gacactgacc     360

tccgggatca tgttcattgt ctcaggtctt tgtgcaattg ctggagtgtc tgtgtttgcc     420

aacatgctgg tgactaactt ctggatgtcc acagctaaca tgtacaccgg catgggtggg     480

atggtgcaga ctgttcagac caggtacaca tttggtgcgg ctctgttcgt gggctgggtc     540

gctggaggcc tcacactaat tgggggtgtg atgatgtgca tcgcctgccg gggcctggca     600

ccagaagaaa ccaactacaa agccgtttct tatcatgcct cgggccacag tgttgcctac     660

aagcctggag gcttcaaggc cagcactggc tttgggtcca acaccaaaaa caagaagata     720

tacgatggag gtgcccgcac agaggacgag gtacaatctt atccttccaa gcacgactat     780

gtgtaa                                                                786


<210> SEQ ID NO 5
<211> LENGTH: 786
<212> TYPE: DNA
<213> ORGANISM: Artificial Sequence
<220> FEATURE:
<223> OTHER INFORMATION: Synthetic Sequence

<400> SEQUENCE: 5
```

atgtccacca ccacatgcca agtggtggcg ttcctcctgt ccatcctggg gctggccggc 60
tgcatcgcgg ccaccgggat ggacatgtgg agcacccagg acctgtacga caaccccgtc 120
acctccgtgt tccagtacga agggctctgg aggagctgcg tgaggcagag ttcaggcttc 180
accgaatgca ggccctattt caccatcctg ggacttccag ccatgctgca ggcagtgcga 240
gccctgatga tcgtaggcat cgtcctgggt gccattggcc tcctggtatc catctttgcc 300
ctgaaatgca tccgcattgg cagcatggag gactctgcca aagccaacat gacactgacc 360
tccgggatca tgttcattgt ctcaggtctt tgtgcaattg ctggagtgtc tgtgtttgcc 420
aacatgctgg tgactaactt ctggatgtcc acagctaaca tgtacaccgg catgggtggg 480
atggtgcaga ctgttcagac caggtacaca tttggtgcgg ctctgttcgt gggctgggtc 540
gctggaggcc tcacactaat tgggggtgtg atgatgtgca tcgcctgccg gggcctggca 600
ccagaagaaa ccaactacaa agccgtttct tatcatgcct caggccacag tgttgcctac 660
aagcctggag gcttcaaggc cagcactggc tttgggtcca acaccaaaaa caagaagata 720
tacgatggag gtgcccgcac agaggacgag gtacaatctt atccttccaa gcacgactat 780
gtgtaa 786

<210> SEQ ID NO 6
<211> LENGTH: 795
<212> TYPE: DNA
<213> ORGANISM: Artificial Sequence
<220> FEATURE:
<223> OTHER INFORMATION: Synthetic Sequence

<400> SEQUENCE: 6
atgtcggtga ccgcctgcca gggcttgggg tttgtggtgt cactgatcgg gtttgcgggc 60
atcattgcag ccacttgtat ggaccagtgg agcacccagg atttatacaa caacccggtg 120
accgctgtat tcaactacca agggctatgg cgttcatgcg tccgagagag ctctggcttc 180
accgagtgcc gaggctactt caccctgttg gggttgccag ccatgctgca agctgtacga 240
gccctgatga tcgtgggcat tgttctgggg gtcatcggta tcctcgtgtc catcttcgcc 300
ctgaagtgca ttcgcattgg tagcatggat gactctgcca aggccaagat gactctgact 360
tctgggatct tgttcatcat ctccggcatc tgtgcaatca ttggtgtgtc tgtgtttgcc 420
aacatgctgg tgaccaactt ctggatgtcc acagctaaca tgtacagcgg catgggcggc 480
atgggtggca tggtgcagac cgttcagacc aggtacacct ttggtgcagc tctgttcgtg 540
ggctgggttg ctggaggcct caccctgatt gggggagtga tgatgtgcat cgcctgccgt 600
ggcctgacac cagatgacag caacttcaaa gctgtgtctt accatgcctc tggccaaaat 660
gttgcctaca ggcctggagg ctttaaggcc agcactggct ttgggtccaa caccagaaac 720
aagaagatct acgatggggg tgcccgcaca gaagacgatg aacagtctca tcctaccaag 780
tatgactatg tgtag 795

<210> SEQ ID NO 7
<211> LENGTH: 795
<212> TYPE: DNA
<213> ORGANISM: Artificial Sequence
<220> FEATURE:
<223> OTHER INFORMATION: Synthetic Sequence

<400> SEQUENCE: 7
atggccacca ccacgtgcca ggtggtaggg cttctcctgt ccctcctggg tctggccggc 60
tgcatagccg ccactgggat ggacatgtgg agcactcaag acctgtatga caacccagtc 120
accgccgtgt tccagtatga agggctctgg aggagttgcg tgcaacagag ctcggggttc 180
accgagtgcc ggccatactt caccatcctg ggccttccag ccatgctgca agctgtacga 240
gccctgatga tcgtgggcat tgttctgggg gtcatcggta tcctcgtgtc catcttcgcc 300
ctgaagtgca ttcgcattgg tagcatggat gactctgcca aggccaagat gactctgact 360
tctgggatct tgttcatcat ctccggcatc tgtgcaatca ttggtgtgtc tgtgtttgcc 420
aacatgctgg tgaccaactt ctggatgtcc acagctaaca tgtacagcgg catgggcggc 480
atgggtggca tggtgcagac cgttcagacc aggtacacct ttggtgcagc tctgttcgtg 540
ggctgggttg ctggaggcct caccctgatt gggggagtga tgatgtgcat cgcctgccgt 600
ggcctgacac cagatgacag caacttcaaa gctgtgtctt accatgcctc tggccaaaat 660
gttgcctaca ggcctggagg ctttaaggcc agcactggct ttgggtccaa caccagaaac 720
aagaagatct acgatggggg tgcccgcaca gaagacgatg aacagtctca tcctaccaag 780
tatgactatg tgtag 795

<210> SEQ ID NO 8
<211> LENGTH: 1401
<212> TYPE: DNA
<213> ORGANISM: Artificial Sequence
<220> FEATURE:
<223> OTHER INFORMATION: Synthetic Sequence

<400> SEQUENCE: 8
atggaatgga cctgggtctt tctcttcctc ctgtcagtaa ctgcaggtgt ccactcccag 60
gttcagctgc agcagtctgg agctgagctg atgaagcctg gggcctcagt gaagatatcc 120
tgcaaggcta ctggctacac attcagtagc tactggatag agtgggtaaa gcagaggcct 180
ggacatggcc ttgagtggat tggagagatt ttacctggaa gtggtagtac taactacaat 240
gagaagttca agggcaaggc cacattcact gcagatacat cctccaacac agcctacatg 300
caactcagca gcctgacatc tgaggactct gccgtctatt actgtgcaag atatgattac 360
ccctggtttg cttactgggg ccaagggact ctggtcactg tctctgcagc ctctacaaag 420
ggccccagcg tgtttccact ggctccctcc tctaagagca caagcggcgg caccgctgcc 480
ctgggctgtc tggtgaagga ctactttcca gagcctgtga cagtgagctg gaattccggc 540
gctctgacct ctggcgtgca cacctttcca gccgtgctgc agtcttccgg cctgtactcc 600
ctgtctagcg tggtgaccgt gcccagctcc tctctgggca cccagacata tatctgcaac 660
gtgaatcaca agccttccaa tacaaaggtg gacaagaagg tggagccaaa gtcctgtgac 720
aagacccata catgcccccc atgtcctgct cccgagctgc tgggcggccc ttccgtgttc 780
ctgtttcccc caaagcccaa ggataccctg atgatcagca gaaccccaga ggtgacatgc 840
gtggtggtgg acgtgtccca tgaggatccc gaggtgaagt tcaactggta cgtggacggc 900
gtggaggtgc ataacgccaa gacaaagcct agagaggagc agtacaactc cacctaccgg 960
gtggtgtccg tgctgaccgt gctgcaccag gactggctga atggcaagga gtacaagtgc 1020
aaggtgtcta ataaggccct gcctgctcca atcgagaaga caatctctaa ggctaagggc 1080
cagcctcggg agccccaggt gtataccctg cctccatcca gagacgagct gaccaagaat 1140
caggtgtctc tgacatgcct ggtgaagggc ttctatccat ccgatatcgc tgtggagtgg 1200
gagagcaatg gccagcctga gaacaattat aagacaaccc cacctgtgct ggattctgac 1260
ggcagctttt tcctgtattc caagctgacc gtggataagt ctagatggca gcagggcaac 1320
gtgttctcct gtagcgtgat gcacgaggca ctgcataatc actacaccca gaagtcactg 1380
tcactgagtc caggcaaata a 1401

<210> SEQ ID NO 9
<211> LENGTH: 708
<212> TYPE: DNA
<213> ORGANISM: Artificial Sequence
<220> FEATURE:
<223> OTHER INFORMATION: Synthetic Sequence

<400> SEQUENCE: 9 atgcatttc aagtgcagat tttcagcttc ctgctaatca gtgcctcagt cataatgtcc 60
agaggacaaa ttgttctcac ccagtctcca gcaatcatgt ctgcatctcc aggggagaag 120
gtcaccataa cctgcagtgc cagctcaagt gtaagttaca tgcactggtt ccagcagaag 180
ccaggcactt ctcccaaact ctggatttat agcacatcca acctggcttc tggagtccct 240
gctcgcttca gtggcagtgg atctgggacc tcttactctc tcacaatcag ccgaatggag 300
gctgaagatg ctgccactta ttactgccag caaaggagta gttacccacc cacgttcgga 360 gggggacca agctggaaat aaagagaacc gtggctgccc caagcgtgtt tatcttccct 420
ccatctgatg agcagctgaa gtctggcaca gctagcgtgg tgtgcctgct gaataacttc 480
taccccagag aggccaaggt gcagtggaag gtggataacg ctctgcagtc tggcaactcc 540
caggagtctg tgacagagca ggattccaag gacagcacat actccctgtc tagcaccctg 600
acactgagca aggctgacta cgagaagcac aaggtgtacg cttgcgaggt cactcatcag 660
ggactgtcat ctcctgtcac taagagtttt aatcgcggcg agtgttga 708

<210> SEQ ID NO 10
<211> LENGTH: 1404
<212> TYPE: DNA
<213> ORGANISM: Artificial Sequence
<220> FEATURE:
<223> OTHER INFORMATION: Synthetic Sequence

<400> SEQUENCE: 10
atgggatgga gctgtatcat cctcttcttg gtagcaacag ctacaggtgt ccactcccag 60
gtccaactgc agcagcctgg ggctgagctg gtgaggcctg gggcttcagt gaagctgtcc 120
tgcaaggctt ctggctacac cttcaccagc tactggataa actgggtgaa gcagaggcct 180
ggacaaggcc ttgagtggat cggaaatatt tatccttctg atagttatac taactacaat 240
caaaagttca aggacaaggc cacattgact gtagacaaat cctccagcac agcctacatg 300
cagctcagca gcccgacatc tgaggactct gcggtctatt actgtacaag atcgtggagg 360
ggtaactcct ttgactactg gggccaaggc accactctca cagtctcctc agcctctaca 420
aagggcccca gcgtgtttcc actggctccc tcctctaaga gcacaagcgg cggcaccgct 480
gccctgggct gtctggtgaa ggactacttt ccagagcctg tgacagtgag ctggaattcc 540
ggcgctctga cctctggcgt gcacaccttt ccagccgtgc tgcagtcttc cggcctgtac 600
tccctgtcta gcgtggtgac cgtgcccagc tcctctctgg gcacccagac atatatctgc 660
aacgtgaatc acaagccttc caatacaaag gtggacaaga aggtggagcc aaagtcctgt 720
gacaagaccc atacatgccc cccatgtcct gctcccgagc tgctgggcgg cccttccgtg 780
ttcctgtttc ccccaaagcc caaggatacc ctgatgatca gcagaacccc agaggtgaca 840
tgcgtggtgg tggacgtgtc ccatgaggat cccgaggtga agttcaactg gtacgtggac 900
ggcgtggagg tgcataacgc caagacaaag cctagagagg agcagtacaa ctccacctac 960
cgggtggtgt ccgtgctgac cgtgctgcac caggactggc tgaatggcaa ggagtacaag 1020
tgcaaggtgt ctaataaggc cctgcctgct ccaatcgaga agacaatctc taaggctaag 1080
ggccagcctc gggagcccca ggtgtatacc ctgcctccat ccagagacga gctgaccaag 1140
aatcaggtgt ctctgacatg cctggtgaag ggcttctatc catccgatat cgctgtggag 1200
tgggagagca atggccagcc tgagaacaat tataagacaa ccccacctgt gctggattct 1260
gacggcagct ttttcctgta ttccaagctg accgtggata agtctagatg gcagcagggc 1320
aacgtgttct cctgtagcgt gatgcacgag gcactgcata atcactacac ccagaagtca 1380
ctgtcactga gtccaggcaa ataa 1404

<210> SEQ ID NO 11
<211> LENGTH: 723
<212> TYPE: DNA
<213> ORGANISM: Artificial Sequence
<220> FEATURE:
<223> OTHER INFORMATION: Synthetic Sequence

<400> SEQUENCE: 11
atggaatcac agactcaggt cctcatgtcc ctgctgttct gggtatctgg tacctgtggg 60
gacattgtga tgacacagtc tccatcctcc ctgactgtga cagcaggaga gaaggtcact 120
atgagctgca agtccagtca gagtctgtta aacagtggaa atcaaaagaa ctacttgacc 180
tggtaccagc agaaaccagg gcagcctcct aaactgttga tctactgggc atccactagg 240
gaatctgggg tccctgatcg cttcacaggc agtggatctg gaacagattt cactctcacc 300
atcagcagtg tgcaggctga agacctggca gtttattact gtcagaatga ttatagttat 360
ccattcacgt tcggctcggg gacaaagttg gaaataaaga gaaccgtggc tgccccaagc 420
gtgtttatct tccctccatc tgatgagcag ctgaagtctg gcacagctag cgtggtgtgc 480
ctgctgaata acttctaccc cagagaggcc aaggtgcagt ggaaggtgga taacgctctg 540
cagtctggca actcccagga gtctgtgaca gagcaggatt ccaaggacag cacatactcc 600
ctgtctagca ccctgacact gagcaaggct gactacgaga agcacaaggt gtacgcttgc 660
gaggtcactc atcagggact gtcatctcct gtcactaaga gttttaatcg cggcgagtgt 720
tga 723

<210> SEQ ID NO 12
<211> LENGTH: 1404
<212> TYPE: DNA
<213> ORGANISM: Artificial Sequence
<220> FEATURE:
<223> OTHER INFORMATION: Synthetic Sequence

<400> SEQUENCE: 12
atggattggc tgtggaactt gctattcctg atggcagctg cccaaagtat ccaagcacag 60
atccagttgg tgcagtctgg acctgagctg aagaagcctg gagagacagt caagatctcc 120
tgcaaggctt ctgggtatac cttcacaaac tatggaatga actgggtgaa gcaggctcca 180
ggaaagggtt taaagtggat gggctggata aacaccaaca ctggagagcc aacatatgct 240
gaagagttca agggacggtt tgccttctct ttggaaacct ctgccagcac tgcctatttg 300
cagatcaaca acctcaaaaa tgaggacacg gctacatatt tctgtgcaag actgggtttt 360
ggtaatgcta tggactactg gggtcaagga acctcagtca ccgtctcctc agcctctaca 420
aagggcccca gcgtgtttcc actggctccc tcctctaaga gcacaagcgg cggcaccgct 480

```
gccctgggct gtctggtgaa ggactacttt ccagagcctg tgacagtgag ctggaattcc    540

ggcgctctga cctctggcgt gcacaccttt ccagccgtgc tgcagtcttc cggcctgtac    600

tccctgtcta gcgtggtgac cgtgcccagc tcctctctgg gcacccagac atatatctgc    660

aacgtgaatc acaagccttc caatacaaag gtggacaaga aggtggagcc aaagtcctgt    720

gacaagaccc atacatgccc cccatgtcct gctcccgagc tgctgggcgg cccttccgtg    780

ttcctgtttc cccccaaagcc caaggatacc ctgatgatca gcagaacccc agaggtgaca    840

tgcgtggtgg tggacgtgtc ccatgaggat cccgaggtga agttcaactg gtacgtggac    900

ggcgtggagg tgcataacgc caagacaaag cctagagagg agcagtacaa ctccacctac    960

cgggtggtgt ccgtgctgac cgtgctgcac caggactggc tgaatggcaa ggagtacaag   1020

tgcaaggtgt ctaataaggc cctgcctgct ccaatcgaga agacaatctc taaggctaag   1080

ggccagcctc gggagcccca ggtgtatacc ctgcctccat ccagagacga gctgaccaag   1140

aatcaggtgt ctctgacatg cctggtgaag ggcttctatc catccgatat cgctgtggag   1200

tgggagagca atggccagcc tgagaacaat tataagacaa ccccacctgt gctggattct   1260

gacggcagct tttcctgta ttccaagctg accgtggata agtctagatg gcagcagggc    1320

aacgtgttct cctgtagcgt gatgcacgag gcactgcata atcactacac ccagaagtca   1380

ctgtcactga gtccaggcaa ataa                                          1404
```

<210> SEQ ID NO 13
<211> LENGTH: 723
<212> TYPE: DNA
<213> ORGANISM: Artificial Sequence
<220> FEATURE:
<223> OTHER INFORMATION: Synthetic Sequence

<400> SEQUENCE: 13

```
atggaatcac agactcaggt cctcatgtcc ctgctgttct gggtatctgg tacctgtggg     60

gacattgtga tgacacagtc tccatcctcc ctgactgtga cagcaggaga gaaggtcact    120

atgagctgca agtccagtca gagtctgtta aacagtggaa atcaaaagaa ctacttgacc    180

tggtaccagc agaaaccagg gcagcctcct aaactgttga tctactgggc atccactagg    240

gaatctgggg tccctgatcg cttcacaggc agtggatctg gaacagattt cactctcacc    300

atcagcagtg tgcaggctga agacctggca gtttattact gtcagaatga ttatagttat    360

ccgctcacgt tcggtgctgg gaccaagctg gagctgaaga gaaccgtggc tgccccaagc    420

gtgtttatct tccctccatc tgatgagcag ctgaagtctg gcacagctag cgtggtgtgc    480

ctgctgaata acttctaccc cagagaggcc aaggtgcagt ggaaggtgga taacgctctg    540

cagtctggca actcccagga gtctgtgaca gagcaggatt ccaaggacag cacatactcc    600

ctgtctagca ccctgacact gagcaaggct gactacgaga agcacaaggt gtacgcttgc    660

gaggtcactc atcagggact gtcatctcct gtcactaaga gttttaatcg cggcgagtgt    720

tga                                                                  723
```

<210> SEQ ID NO 14
<211> LENGTH: 354
<212> TYPE: DNA
<213> ORGANISM: Artificial Sequence
<220> FEATURE:
<223> OTHER INFORMATION: Synthetic Sequence

<400> SEQUENCE: 14
gagatccagc tgcagcagtc tggagctgag ctggtgaagc ctggggcttc agtgaagata 60
tcctgcaagg ctcctggtta ctcattcact gactacaata tgaactgggt gaagcagagc 120
catggaaaga gccttgagtg gattggaaat attaattctt actatggtag tactagctac 180
aatcagaagt tcaagggcaa ggccacattg actgtagaca gatcttccag cacagcctac 240
atgcagctca acagcctgac atctgaggac tctgcagtct attactgtac aaacttcgac 300
aggggaaatt cgttccctta ctggggccac gggactctgg tcactgtctc tgca 354

<210> SEQ ID NO 15
<211> LENGTH: 354
<212> TYPE: DNA
<213> ORGANISM: Artificial Sequence
<220> FEATURE:
<223> OTHER INFORMATION: Synthetic Sequence

<400> SEQUENCE: 15
gaggtgaaac tggtggagtc tgggggaggc ttagtgaagc ctggagggtc cctgaaactc 60
tcctgtgcag cctctggatt cactatcagt gactacggaa tggcgtgggt tcgacaggct 120
ccagggaagg ggcctgagtg ggtagcattc attagtaatt tggcatatag tatccactat 180
gtagacactg tgacgggccg attcaccatc tctagagaga atgccaagaa caccctgtac 240
ctggaaatgc gtagtctgag gtctgaggac acagccatgt attactgtgc aagaatgtac 300
tatgggaatg ctttggacta ctggggtcaa ggaacctcag tcaccgtctc ctca 354

<210> SEQ ID NO 16
<211> LENGTH: 339
<212> TYPE: DNA
<213> ORGANISM: Artificial Sequence
<220> FEATURE:
<223> OTHER INFORMATION: Synthetic Sequence

<400> SEQUENCE: 16
gacattgtga tgacacagtc tccatcctcc ctgactgtga cagtaggaga gaaggtcact 60
atgacctgca agtccagtca gagtctgtta aacagtggaa atcaaaagaa ctatttgacc 120
tggtaccagc agaaaccagg gcagtctcct aaactgttga tctactgggc atccactagg 180
gaatctgggg tccctgagcg cttcacaggc agaggatctg gaacagattt cactctcacc 240
atcagcagtg tgcaggctga agacctggca gtttattact gtcagaatgg ttatagttat 300
ccattcacgt tcggctcggg gacaaacttg gaaataaaa 339

<210> SEQ ID NO 17
<211> LENGTH: 339
<212> TYPE: DNA
<213> ORGANISM: Artificial Sequence
<220> FEATURE:
<223> OTHER INFORMATION: Synthetic Sequence

<400> SEQUENCE: 17
gacattgtga tgacacagtc tccatcctcc ctgactgtga caacaggaga gaaggtcact 60
atgagttgca agtccagtca gaatctgtta aacagtggaa atcaaaagaa ctacttgacc 120
tggtaccagc agaaaccagg gcagcctcct aaactgttga tctactgggc atccactagg 180
gaatctgggg tccctgatcg cttcacaggc agtggatctg gaacagattt cactctcacc 240
atcagcagtg tgcaggctga agacctggca gtttattact gtcagaatga ttatagtttt 300
cctctcacgt tcggtgctgg gaccaagctg gagctgaaa 339

<210> SEQ ID NO 18
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 18

Gly Tyr Ser Phe Thr Asp Tyr
1 5

<210> SEQ ID NO 19
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 19

Asn Ser Tyr Tyr Gly Ser
1 5

<210> SEQ ID NO 20
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 20

Phe Asp Arg Gly Asn Ser Phe Pro Tyr
1 5

<210> SEQ ID NO 21
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 21

Gly Phe Thr Ile Ser Asp Tyr
1 5

<210> SEQ ID NO 22
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 22

Ser Asn Leu Ala Tyr Ser
1 5

<210> SEQ ID NO 23
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 23

Met Tyr Tyr Gly Asn Ala Leu Asp Tyr
1 5

<210> SEQ ID NO 24

<211> LENGTH: 17
<212> TYPE: PRT
<213> ORGANISM: Artificial Sequence
<220> FEATURE:
<223> OTHER INFORMATION: Synthetic Sequence

<400> SEQUENCE: 24

Lys Ser Ser Gln Ser Leu Leu Asn Ser Gly Asn Gln Lys Asn Tyr Leu
1 5 10 15

Thr

<210> SEQ ID NO 25
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 25

Trp Ala Ser Thr Arg Glu Ser
1 5

<210> SEQ ID NO 26
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 26

Gln Asn Gly Tyr Ser Tyr Pro Phe Thr
1 5

<210> SEQ ID NO 27
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 27

Lys Ser Ser Gln Asn Leu Leu Asn Ser Gly Asn Gln Lys Asn Tyr Leu
1 5 10 15

Thr

<210> SEQ ID NO 28
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 28

Trp Ala Ser Thr Arg Glu Ser
1 5

<210> SEQ ID NO 29
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 29

Gln Asn Asp Tyr Ser Phe Pro
1 5

<210> SEQ ID NO 30
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 30

```
Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105
```

<210> SEQ ID NO 31
<211> LENGTH: 329
<212> TYPE: PRT
<213> ORGANISM: Artificial Sequence
<220> FEATURE:
<223> OTHER INFORMATION: Synthetic Sequence

<400> SEQUENCE: 31

```
Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Met Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val Leu Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
```

```
        195                 200                 205

Lys Ala Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly
                325
```

<210> SEQ ID NO 32
<211> LENGTH: 1401
<212> TYPE: DNA
<213> ORGANISM: Artificial Sequence
<220> FEATURE:
<223> OTHER INFORMATION: Synthetic Sequence

<400> SEQUENCE: 32

```
atgggctgga gctgcatcat cctctttctg gtggctactg ctaccggcgt gcactccgag     60

attcaactcc agcagagcgg agccgagctg gtgaaacccg gcgcctccgt caaaatcagc    120

tgcaaagccc ccggatacag cttcaccgac tacaacatga actgggtcaa gcagtcccac    180

ggcaagtctc tggagtggat cggcaacatc aacagctact acggatccac ctcctacaac    240

cagaagttca agggcaaggc caccctcacc gtggataggt ccagctccac cgcctacatg    300

cagctgaact ccctcaccag cgaagactcc gctgtgtact actgcaccaa cttcgacaga    360

ggcaacagct ttccctattg ggacatggaa actctggtca ccgtgagcgc cgccaaaacc    420

accgctccta gcgtctaccc cctcgctccc gtgtgtggcg acaccactgg aagctccgtg    480

actctgggct gtctcgtgaa gggatacttc cccgagcccg tgactctgac ttggaattcc    540

ggctctctga gctccggcgt ccacactttc cccgccgtgc tgcagtccga tctgtacact    600

ctgagcagca gcgtgaccgt cacctccagc acttggcctt cccagtccat cacttgcaac    660

gtggctcacc ccgccagcag caccaaggtc gacaagaaga tcgagcctag gggacccact    720

atcaaacctt gccctccttg caaatgtccc gcccccaatc tgctgggcgg acccagcgtg    780

ttcatcttcc cccccaagat caaggacgtg ctcatgatct ctctgagccc catggtgact    840

tgcgtcgtgg tcgacgtctc cgaggatgat cccgacgtgc agattagctg gttcgtgaac    900

aacgtcgagg tcctgactgc tcagacccaa acccataggg aggactacaa ctccactctg    960

agggtcgtca gcgctctgcc cattcagcac caagactgga tgtccggaaa ggagttcaag   1020

tgcaaggtca acaacaaggc tctccccgcc cccatcgaga gaaccatcag caaacccaag   1080

ggcagcgtga gagctcctca agtgtatgtg ctgccccccc ccgaagaaga gatgactaag   1140

aagcaagtga ccctcacttg catggtcacc gatttcatgc ccgaggacat ctacgtggag   1200

tggaccaaca acggcaagac cgagctcaat tacaaaaaca ccgagcccgt gctggacagc   1260

gacggctcct actttatgta ctccaagctg agggtggaga agaagaactg ggtcgagaga   1320
```

aactcctaca gctgctccgt ggtccatgag ggactgcaca accaccatac caccaagtcc 1380
ttctccagaa ctcccggcta a 1401

<210> SEQ ID NO 33
<211> LENGTH: 1401
<212> TYPE: DNA
<213> ORGANISM: Artificial Sequence
<220> FEATURE:
<223> OTHER INFORMATION: Synthetic Sequence

<400> SEQUENCE: 33
atgggctgga gctgtatcat cctctttctg gtcgccaccg ctaccggagt ccactccgag 60
gtcaagctcg tggaaagcgg aggcggactg gtgaagcccg gcggcagcct caagctgagc 120
tgcgccgctt ccggctttac catcagcgac tatggcatgg cttgggtcag acaagccccc 180
ggcaaaggac ccgagtgggt ggccttcatc agcaacctcg cctattccat ccactacgtc 240
gataccgtca ccggaaggtt caccatttct agggagaacg ccaagaacac tctgtatctg 300
gagatgaggt ctctgagaag cgaggatacc gccatgtact attgcgctag gatgtattac 360
ggaaacgctc tggactactg gggccaaggc acctccgtca ctgtgtcctc cgccaagacc 420
actgctccta gcgtgtatcc tctggctccc gtgtgcggag acactaccgg aagcagcgtc 480
actctgggat gcctcgtcaa aggctacttc cccgagcccg tcactctgac ttggaactcc 540
ggatctctga gcagcggagt ccacaccttt cccgccgtcc tccaaagcga tctgtacact 600
ctgagctcca gcgtgactgt cacttccagc acttggccca gccagagcat cacttgcaac 660
gtcgcccacc ccgccagctc caccaaggtc gacaagaaga tcgaacccag aggacctacc 720
atcaagcctt gccctccttg caaatgcccc gctcctaatc tgctcggagg acccagcgtc 780
ttcattttcc cccccaagat caaagacgtg ctcatgatct ctctgagccc catggtcact 840
tgcgtcgtgg tcgacgtctc cgaagatgac cccgatgtcc agatcagctg gttcgtcaac 900
aacgtggaag tcctgaccgc ccagacccag acccataggg aagactacaa ctccactctg 960
agagtcgtca gcgctctgcc cattcagcac caagactgga tgtccggaaa ggagttcaag 1020
tgcaaggtca acaacaaggc tctgcccgcc cccatcgaga ggaccattag caagcctaag 1080
ggctccgtga gagcccctca agtgtacgtc ctccctcctc ccgaggaaga gatgaccaag 1140
aagcaagtga ctctgacttg catggtgacc gactttatgc ccgaggatat ctacgtcgag 1200
tggaccaaca acggcaagac cgagctcaac tacaagaata ccgagcccgt gctggacagc 1260
gacggctcct actttatgta ctccaagctg agggtcgaga agaaaaactg ggtggagaga 1320
aattcctaca gctgctccgt cgtgcatgag ggactgcaca accaccatac cactaagagc 1380
ttctctagga ctcccggata a 1401

<210> SEQ ID NO 34
<211> LENGTH: 723
<212> TYPE: DNA
<213> ORGANISM: Artificial Sequence
<220> FEATURE:
<223> OTHER INFORMATION: Synthetic Sequence

<400> SEQUENCE: 34
atggagagcc agacccaagt gctgatgtct ctgctcttct gggtcagcgg cacttgcggc 60
gatatcgtca tgactcagtc ccccagctct ctgactgtca ctgtcggcga aaaggtgacc 120
atgacttgca agagcagcca gtccctcctc aattccggca accagaagaa ctacctcact 180

```
tggtaccagc agaagcccgg acagagccct aagctgctga tctactgggc ctccactaga    240

gagtccggag tgcccgagag gtttaccggc agaggctccg gcaccgattt caccctcacc    300

atcagcagcg tgcaagccga ggatctggcc gtctactact gccagaacgg atactcctac    360

cccttcacct tcggctccgg cactaatctg gagatcaaaa gagccgacgc cgctcccacc    420

gtcagcatct tccctcctag ctccgagcaa ctgacttccg gcggagccag cgtggtgtgc    480

tttctgaaca acttctatcc caaagacatt aacgtcaagt ggaagatcga tggcagcgag    540

aggcagaatg gcgtgctgaa cagctggact gaccaagata gcaaagactc cacctactcc    600

atgagctcca ccctcactct caccaaggat gagtacgaga ggcacaactc ctacacttgc    660

gaagccaccc acaagacctc caccagcccc atcgtgaaga gcttcaatag gaacgagtgc    720

taa                                                                  723
```

```
<210> SEQ ID NO 35
<211> LENGTH: 723
<212> TYPE: DNA
<213> ORGANISM: Artificial Sequence
<220> FEATURE:
<223> OTHER INFORMATION: Synthetic Sequence

<400> SEQUENCE: 35

atggagtccc agacccaagt gctgatgtct ctgctgtttt gggtcagcgg aacttgcggc     60

gatatcgtca tgactcagag ccccagcagc ctcaccgtga ctactggcga aaaggtcacc    120

atgagctgca aaagcagcca gaacctcctc aacagcggca accagaagaa ctacctcact    180

tggtaccagc agaagcccgg acagcccccct aagctcctca tctactgggc cagcactagg    240

gagagcggag tgcccgatag gttcaccggc agcggaagcg gcaccgattt cactctgact    300

atcagctccg tgcaagccga agatctggcc gtctactact gccagaacga ctactccttc    360

cctctgacct tcggagccgg aaccaagctc gagctgaaga gagccgatgc cgcccccact    420

gtcagcatct ttcctcccag ctccgaacag ctgactagcg gaggcgcctc cgtggtgtgc    480

ttcctcaaca acttctatcc caaagatatc aacgtcaagt ggaagatcga cggcagcgag    540

agacagaacg gcgtgctgaa cagctggacc gaccaagata gcaaggactc cacttatagc    600

atgagcagca ctctgactct gactaaggac gagtatgaga ggcacaactc ctacacttgc    660

gaggccactc acaaaacctc cacctccccc atcgtcaagt ccttcaatag gaacgagtgt    720

taa                                                                  723
```

```
<210> SEQ ID NO 36
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 36

Glu Ile Gln Leu Gln Gln Ser Gly Ala Glu Leu Val Lys Pro Gly Ala
1               5                   10                  15

Ser Val Lys Ile Ser Cys Lys Ala Pro Gly Tyr Ser Phe Thr Asp Tyr
            20                  25                  30

Asn Met Asn Trp Val Lys Gln Ser His Gly Lys Ser Leu Glu Trp Ile
        35                  40                  45

Gly Asn Ile Asn Ser Tyr Tyr Gly Ser Thr Ser Tyr Asn Gln Lys Phe
    50                  55                  60

Lys Gly Lys Ala Thr Leu Thr Val Asp Arg Ser Ser Ser Thr Ala Tyr
```

```
65                  70                  75                  80

Met Gln Leu Asn Ser Leu Thr Ser Glu Asp Ser Ala Val Tyr Tyr Cys
                85                  90                  95

Thr Asn Phe Asp Arg Gly Asn Ser Phe Pro Tyr Trp Gly His Gly Thr
            100                 105                 110

Leu Val Thr Val Ser Ala
        115


<210> SEQ ID NO 37
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 37

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Ile Ser Asp Tyr
            20                  25                  30

Gly Met Ala Trp Val Arg Gln Ala Pro Gly Lys Gly Pro Glu Trp Val
        35                  40                  45

Ala Phe Ile Ser Asn Leu Ala Tyr Ser Ile His Tyr Val Asp Thr Val
    50                  55                  60

Thr Gly Arg Phe Thr Ile Ser Arg Glu Asn Ala Lys Asn Thr Leu Tyr
65                  70                  75                  80

Leu Glu Met Arg Ser Leu Arg Ser Glu Asp Thr Ala Met Tyr Tyr Cys
                85                  90                  95

Ala Arg Met Tyr Tyr Gly Asn Ala Leu Asp Tyr Trp Gly Gln Gly Thr
            100                 105                 110

Ser Val Thr Val Ser Ser
        115


<210> SEQ ID NO 38
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 38

Asp Ile Val Met Thr Gln Ser Pro Ser Ser Leu Thr Val Thr Val Gly
1               5                   10                  15

Glu Lys Val Thr Met Thr Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Glu Arg Phe Thr Gly Arg Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Gly Tyr Ser Tyr Pro Phe Thr Phe Gly Ser Gly Thr Asn Leu Glu Ile
            100                 105                 110

Lys
```

<210> SEQ ID NO 39
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 39

```
Asp Ile Val Met Thr Gln Ser Pro Ser Ser Leu Thr Val Thr Thr Gly
1               5                   10                  15

Glu Lys Val Thr Met Ser Cys Lys Ser Ser Gln Asn Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Phe Pro Leu Thr Phe Gly Ala Gly Thr Lys Leu Glu Leu
            100                 105                 110

Lys
```

<210> SEQ ID NO 40
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 40

```
Glu Ile Gln Leu Gln Gln Ser Gly Ala Glu Leu Val Lys Pro Gly Ala
1               5                   10                  15

Ser Val Lys Ile Ser Cys Lys Ala Pro
            20                  25
```

<210> SEQ ID NO 41
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 41

```
Asn Met Asn Trp Val Lys Gln Ser His Gly Lys Ser Leu Glu Trp Ile
1               5                   10                  15

Gly Asn Ile
```

<210> SEQ ID NO 42
<211> LENGTH: 41
<212> TYPE: PRT
<213> ORGANISM: Artificial Sequence
<220> FEATURE:
<223> OTHER INFORMATION: Synthetic Sequence

<400> SEQUENCE: 42

```
Thr Ser Tyr Asn Gln Lys Phe Lys Gly Lys Ala Thr Leu Thr Val Asp
1               5                   10                  15

Arg Ser Ser Ser Thr Ala Tyr Met Gln Leu Asn Ser Leu Thr Ser Glu
            20                  25                  30
```

```
Asp Ser Ala Val Tyr Tyr Cys Thr Asn
        35                  40


<210> SEQ ID NO 43
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 43

Trp Gly His Gly Thr Leu Val Thr Val Ser Ala
1               5                   10


<210> SEQ ID NO 44
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 44

Glu Val Lys Leu Val Glu Ser Gly Gly Gly Leu Val Lys Pro Gly Gly
1               5                   10                  15

Ser Leu Lys Leu Ser Cys Ala Ala Ser
            20                  25


<210> SEQ ID NO 45
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 45

Gly Met Ala Trp Val Arg Gln Ala Pro Gly Lys Gly Pro Glu Trp Val
1               5                   10                  15

Ala Phe Ile


<210> SEQ ID NO 46
<211> LENGTH: 41
<212> TYPE: PRT
<213> ORGANISM: Artificial Sequence
<220> FEATURE:
<223> OTHER INFORMATION: Synthetic Sequence

<400> SEQUENCE: 46

Ile His Tyr Val Asp Thr Val Thr Gly Arg Phe Thr Ile Ser Arg Glu
1               5                   10                  15

Asn Ala Lys Asn Thr Leu Tyr Leu Glu Met Arg Ser Leu Arg Ser Glu
            20                  25                  30

Asp Thr Ala Met Tyr Tyr Cys Ala Arg
        35                  40


<210> SEQ ID NO 47
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 47

Trp Gly Gln Gly Thr Ser Val Thr Val Ser Ser
1               5                   10
```

<210> SEQ ID NO 48
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 48

Asp Ile Val Met Thr Gln Ser Pro Ser Ser Leu Thr Val Thr Val Gly
1 5 10 15

Glu Lys Val Thr Met Thr Cys
20

<210> SEQ ID NO 49
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 49

Trp Tyr Gln Gln Lys Pro Gly Gln Ser Pro Lys Leu Leu Ile Tyr
1 5 10 15

<210> SEQ ID NO 50
<211> LENGTH: 32
<212> TYPE: PRT
<213> ORGANISM: Artificial Sequence
<220> FEATURE:
<223> OTHER INFORMATION: Synthetic Sequence

<400> SEQUENCE: 50

Gly Val Pro Glu Arg Phe Thr Gly Arg Gly Ser Gly Thr Asp Phe Thr
1 5 10 15

Leu Thr Ile Ser Ser Val Gln Ala Glu Asp Leu Ala Val Tyr Tyr Cys
20 25 30

<210> SEQ ID NO 51
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 51

Phe Gly Ser Gly Thr Asn Leu Glu Ile Lys
1 5 10

<210> SEQ ID NO 52
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 52

Asp Ile Val Met Thr Gln Ser Pro Ser Ser Leu Thr Val Thr Thr Gly
1 5 10 15

Glu Lys Val Thr Met Ser Cys
20

<210> SEQ ID NO 53
<211> LENGTH: 15
<212> TYPE: PRT
<213> ORGANISM: Artificial Sequence

```
<220> FEATURE:
<223> OTHER INFORMATION: Synthetic Sequence

<400> SEQUENCE: 53

Trp Tyr Gln Gln Lys Pro Gly Gln Pro Pro Lys Leu Leu Ile Tyr
1               5                   10                  15


<210> SEQ ID NO 54
<211> LENGTH: 32
<212> TYPE: PRT
<213> ORGANISM: Artificial Sequence
<220> FEATURE:
<223> OTHER INFORMATION: Synthetic Sequence

<400> SEQUENCE: 54

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30


<210> SEQ ID NO 55
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 55

Phe Gly Ala Gly Thr Lys Leu Glu Leu Lys
1               5                   10
```

CLDN18.2 ANTIBODY AND USE THEREOF

TECHNICAL FIELD OF THE APPLICATION

The present application relates to the technical field of antibodies, as well as the use and preparation method of antibodies. Specifically, it relates to a CLDN18.2 antibody and use thereof.

CROSS-REFERENCE TO RELATED APPLICATIONS

This application is the National Stage of International Application No. PCT/CN2021/076481, filed Feb. 10, 2021, which claims the right of priority based on CN Application No. 202010084476.3, filed Feb. 10, 2020.

SEQUENCE LISTING

The application contains a Sequence Listing which has been submitted electronically via EFS-Web and is hereby incorporated by reference in its entirety. Said ASCII copy, created on Apr. 10, 2023, is named 53288US_CRF_sequencelisting.txt and is 42,160 bytes in size.

BACKGROUND OF THE APPLICATION

Claudin is a class of transmembrane proteins with a molecular weight of 20 to 30 kDa. Its family has 24 members which are expressed in many tissues and are important molecules for the formation of tight junctions (TJ) between cells. Epithelial cells or endothelial cells form a highly ordered organization of binding through tight-binding molecules (including Claudin molecules) expressed on the cell surface, that is, tight junctions between cells, which control the flow of molecules in the epithelium space. TJ plays a crucial role in maintaining the stable state of epithelial cells or endothelial cells under normal physiological conditions and maintaining cell polarity. Among them, more striking is claudin 18 (CLDN18), which includes two variants formed by splicing: CLDN18 splice variant 1 (Claudin18.1, CLDN18.1) and CLDN18 splice variant 2 (Claudin 18.2, CLDN 18.2).

Among them, CLDN18.2 (Genbank accession numbers NM_001002026, and NP_001002026) is a transmembrane protein with a molecular weight of 27.8 kDa, and both the N-terminal and C-terminal of the protein are located intracellularly. The main conformation of the protein comprises 4 transmembrane domains (TMD) and 2 extracellular loops (ECL). CLDN18.2 is highly conserved in a variety of mammals, with a full length of 261 amino acids, of which amino acids 1-6 are the N-terminal intracellular domain, amino acids 7-27 are the transmembrane domain 1 (TMD1), amino acids 28-78 are the extracellular loop 1 (ECL1), amino acids 79-99 are the transmembrane domain 2 (TMD2), amino acids 123-144 are the transmembrane domain 3 (TMD3), amino acids 100-122 are the intracellular region connecting TMD2 and TMD3, amino acids 145-167 are the extracellular loop 2 (ECL2), amino acids 168-190 are the transmembrane region 4 (TMD4), and amino acids 191-261 are the C-terminal intracellular region. There is a classical N-glycosylation motif on the asparagine at position 116.

CLDN18.1 and CLDN18.2 differ only in the first 26 amino acids of the N-terminal in the N-terminal-transmembrane region 1-extracellular loop 1 of the protein, and the rest of the sequences are the same.

There is considerable evidence suggesting that CLDN18.2 is highly expressed in tumor cells of stomach, pancreas, esophagus and other tissues, especially in adenocarcinoma subtype tumor cells. In normal tissues, CLDN18.1 is selectively expressed in lung and gastric epithelial cells; CLDN18.2 is only expressed in short-lived gastric glandular epithelial mucosal tissue (differentiated glandular epithelial cells), but not in gastric epithelial stem cells, and differentiated glandular epithelial cells can be continuously replenished by gastric epithelial stem cells. These molecular expression characteristics provide potential for antibody-based treatment of CLDN18.2-related cancers.

The use of companion diagnostics (CDx) methods to select tumor patients with high expression of CLDN18.2 in clinical trials and clinical applications has important guiding significance for guiding the applicable patients of anti-tumor drugs targeting CLDN18.2. In clinical diagnosis of tumor-specific antigens, patient tumor specimens are usually formalin fixed paraffin-embedded (FFPE) tissues, and tumor-specific antigens will change their natural conformation during FFPE processing. In the subsequent antigen retrieval process, special epitopes that are different from the natural conformation will be exposed (Biotech Histochem, 2009, 84(5): 207-215), therefore diagnosis is typically performed by screening for antibodies that bind specifically to cancer-specific antigens on tumor FFPE tissue.

The application relates to the preparation method, screening, sequence and use of an antibody that specifically recognizes CLDN18.2 antigen in tumor and its FFPE tissue.

SUMMARY OF THE APPLICATION

The present application provides a CLDN18.2 antibody for diagnosing cancer, the antibody can recognize CLDN18.2 antigen molecules in fixed tissue samples to diagnose cancer lesions of that including gastric cancer, pancreatic cancer or esophageal cancer. Meanwhile, the CLDN18.2 antibody provided in the present application can also effectively treat cancer lesions of that including gastric cancer, pancreatic cancer or esophageal cancer. Specifically, the application relates to:

1. A CLDN18.2 antibody comprising heavy chain CDRs and light chain CDRs, wherein the heavy chain CDRs are:

CDR1 comprising the sequence as shown in SEQ ID NO:18, CDR2 comprising the sequence as shown in SEQ ID NO:19, and CDR3 comprising the sequence as shown in SEQ ID NO:20; or CDR1 comprising the sequence as shown in SEQ ID NO:21, CDR2 comprising the sequence as shown in SEQ ID NO:22, and CDR3 comprising the sequence as shown in SEQ ID NO:23, wherein the light chain CDRs are:

CDR1 comprising the sequence as shown in SEQ ID NO:24, CDR2 comprising the sequence as shown in SEQ ID NO:25, and CDR3 comprising the sequence as shown in SEQ ID NO:26; or CDR1 comprising the sequence as shown in SEQ ID NO:27, CDR2 comprising the sequence as shown in SEQ ID NO:28, and CDR3 comprising the sequence as shown in SEQ ID NO: 29.

2. The antibody of item 1, comprising a heavy chain variable region as shown in SEQ ID NO:36 or SEQ ID NO:37.

3. The antibody of item 1, comprising a light chain variable region as shown in SEQ ID NO:38 or SEQ ID NO:39.

4. The antibody of any one of items 1-3, comprising a heavy chain variable region as shown in SEQ ID NO:36 and a light chain variable region as shown in SEQ ID NO:38.
5. The antibody of any one of items 1-3, comprising a heavy chain variable region as shown in SEQ ID NO:37 and a light chain variable region as shown in SEQ ID NO:39.
6. The antibody of any one of items 1-5, which is a chimeric antibody, a humanized antibody, or a fully human antibody.
7. The antibody of any one of items 1-6, which is a full-length antibody.
8. The antibody of item 7, which is an IgG antibody.
9. The antibody of any one of items 1-6, which is an antibody fragment that binds to CLDN18.2.
10. The antibody of item 9, which is Fab, Fab'-SH, Fv, scFv or $(Fab')_2$.
11. The antibody of any one of items 1-8, which is a multispecific antibody or a bispecific antibody.
12. The antibody of item 11, wherein the multispecific or bispecific antibody comprises a binding domain that binds to a second biomolecule, wherein the second biomolecule is a cell surface antigen.
13. The antibody of item 12, wherein the cell surface antigen is a tumor antigen.
14. The antibody of item 13, wherein the tumor antigen is selected from the group consisting of: CD3, CD20, FcRH5, HER2, LYPD1, LY6G6D, PMEL17, LY6E, CD19, CD33, CD22, CD79A, CD79B, EDAR, GFRA1, MRP4, RET, Steap1 and TenB2.
15. An immunoconjugate, comprising a therapeutic agent, an agonist of stimulator of interferon genes (STING) receptor, a cytokine, a radionuclide or an enzyme linked to the antibody of any one of items 1-10.
16. The immunoconjugate of item 15, wherein the therapeutic agent is a chemotherapeutic drug.
17. The immunoconjugate of item 15, wherein the therapeutic agent is a cytotoxic agent.
18. A fusion protein or polypeptide comprising the antibody of any one of items 1-10 or an antigen-binding fragment thereof.
19. A pharmaceutical composition comprising the antibody of any one of items 1-14, the immunoconjugate of any one of items 15-17, or the fusion protein or polypeptide of item 18.
20. An isolated nucleic acid comprising a polynucleotide sequence encoding the amino acid sequence of any one of SEQ ID NOs: 18-29.
21. The nucleic acid of item 20, comprising a polynucleotide sequence encoding the amino acid sequence of any one of SEQ ID NOs: 36-39.
22. The nucleic acid of item 21, comprising a polynucleotide sequence encoding the antibody of any one of items 1-10 or an antigen-binding fragment thereof.
23. A vector comprising the polynucleotide sequence of any one of items 20-22.
24. A host cell comprising the polynucleotide sequence of any one of items 20-22 or the vector of item 23.
25. A method for preparing the antibody of any one of items 1-10, comprising culturing the host cell of item 24 and isolating the antibody from the culture.
26. Use of a pharmaceutical composition comprising the antibody of any one of items 1-14, the immunoconjugate of any one of items 15-17, or the fusion protein or polypeptide of item 18 in the preparation of a reagent for diagnosing cancer.
27. Use of a pharmaceutical composition comprising the antibody of any one of items 1-14, the immunoconjugate of any one of items 15-17, or the fusion protein or polypeptide of item 18 in the preparation of a medicament for treating cancer.
28. The use of item 26 or 27, wherein the cancer is gastric cancer, pancreatic cancer or esophageal cancer.
29. A cancer detection reagent comprising the antibody of any one of items 1-10 or an antigen-binding fragment thereof.
30. The cancer detection reagent of item 29, wherein the antibody or antigen-binding fragment thereof is chemically labeled.
31. The cancer detection reagent of item 30, wherein the label is an enzymatic label, a fluorescent label, an isotopic label or a chemiluminescent label.
32. A cancer diagnosis kit comprising the cancer detection reagent of any one of items 29-31.
33. The kit of item 32, wherein the cancer is gastric cancer, pancreatic cancer or esophageal cancer.
34. A method for diagnosing cancer in a subject, comprising contacting the antibody of any one of items 1-14, the fusion protein or polypeptide of item 18, or the detection reagent of any one of items 29-31 with a tissue sample derived from the subject.
35. The diagnostic method of item 34, wherein the tissue sample is body fluid (e.g., blood, and urine) and a tissue section (e.g., tissue biopsy sample) of the subject.
36. The diagnostic method of item 34 or 35, wherein the cancer is selected from gastric cancer, pancreatic cancer or esophageal cancer.
37. A method for treating cancer in a subject, comprising administering to the subject a therapeutically effective amount of the antibody of any one of items 1-14, the immunoconjugate of any one of items 15-17, the fusion protein or polypeptide of item 18, or the pharmaceutical composition of item 19.
38. The treatment method of item 37, wherein the cancer is selected from gastric cancer, pancreatic cancer or esophageal cancer.

DETAIL DESCRIPTION OF THE APPLICATION

1. Definition

Figure 1:
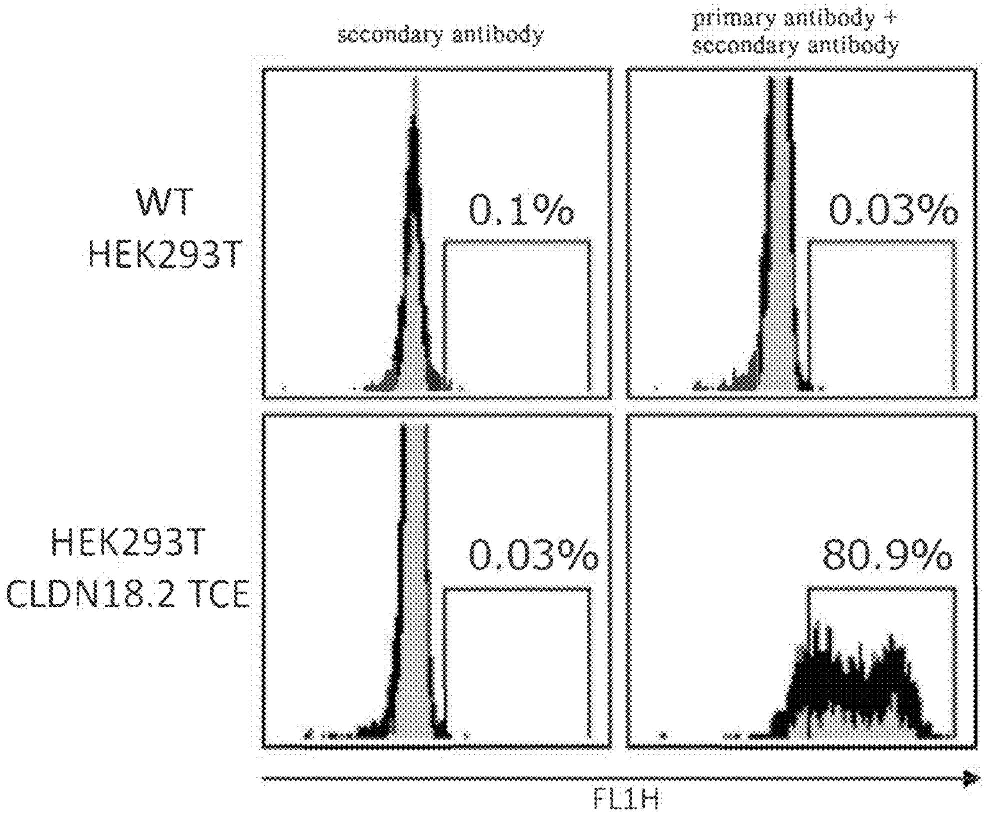
FIG. 1. Transient transfection of HEK293-T cells with human hCLDN18.2-TCE (T-cell epitope peptide) retrovirus expression plasmid.

The term "antibody" is used herein in a broad sense to encompass various antibody structural molecules that bind CLDN18.2 and comprise one or more of the CDR domains disclosed herein, including but not limited to monoclonal antibodies, polyclonal antibodies, multispecific antibodies (e.g., bispecific antibodies) as well as antibody fragments (e.g., Fv, Fab, Fab', Fab'-SH, and $F(ab')_2$), linear antibodies and single chain antibody molecules (e.g., scFv) etc. as long as it exhibits the desired binding activity to CLDN18.2.

Those skilled in the art can fuse one or more CDR domains disclosed in the present application with one or more other polypeptide sequences to prepare functional fusion proteins or polypeptide molecules that bind to CLDN18.2 molecules, such as vaccines, cell membrane receptor antagonists, signaling pathway modulators and chimeric antigen receptor molecules, etc. For example, one or more CDR domains disclosed in the present application can be used to prepare a CLDN18.2 CAR-T (Chimeric Antigen Receptor T-Cell Immunotherapy) molecule. These fusion protein molecules derived and prepared based on the sequence disclosed in the present application are also included in the protection scope of the present application.

The modifier "monoclonal" in the term "monoclonal antibody" as used herein means that the antibody is obtained from a substantially homogeneous population of antibodies, comprising only trace amounts of naturally occurring mutations or those that occur during the preparation of monoclonal antibodies. Compared to polyclonal antibody preparations that typically include different antibodies specific to different epitopes, each monoclonal antibody in a monoclonal antibody preparation is specific to a single epitope on an antigen. Monoclonal antibodies of the application can be made by a variety of techniques including, but not limited to, hybridoma methods, recombinant DNA methods, phage display methods, and methods using transgenic animals comprising all or part of the human immunoglobulin loci.

The terms "full-length antibody" and "intact antibody" refer to an antibody having a structure substantially similar to that of a natural antibody, and the terms are used interchangeably herein.

The "class" of an antibody refers to the type of the constant domain or constant region possessed by its heavy chain. There are five major classes of antibodies: IgA, IgD, IgE, IgG, and IgM, and several of these can be further divided into subclasses (isotypes), e.g., IgG1, IgG2, IgG3, IgG4, IgA1, and IgA2. The heavy chain constant domains corresponding to the different classes of immunoglobulins are called $\alpha$, $\delta$, $\varepsilon$, $\gamma$ and $\mu$, respectively.

A "chimeric antibody" is an antibody having at least a portion of a heavy chain variable region and at least a portion of a light chain variable region derived from one species and at least a portion of a constant region derived from another species. For example, in one embodiment, the chimeric antibody may comprise murine variable regions and human constant regions.

A "humanized" antibody refers to a chimeric antibody comprising amino acid residues from a non-human HVR and amino acid residues from a human FR. In certain embodiments, the humanized antibody comprises at least one, usually two, or substantially an entire variable domain, wherein all or substantially all HVRs (e.g., CDRs) correspond to those of the non-human antibody, and all or substantially all FRs correspond to those of the human antibody. Optionally, the humanized antibody may comprise at least a portion of an antibody constant region derived from the human antibody. A "humanized form" of the antibody (e.g., a non-human antibody) refers to an antibody that has undergone humanization.

A "human common framework" is a framework that represents the amino acid residues most frequently found in the selection of human immunoglobulin VL or VH framework sequences. Generally, human immunoglobulin VL or VH sequences are selected from a subgroup of variable domain sequences. Generally, the subgroup of sequences is as in Kabat et al., Sequences of Proteins of Immunological Interest, 5th edition, NIH Publication 91-3242, Bethesda MD (1991), vols. 1-3. In one embodiment, for VL, the subgroup is subgroup κI as described by Kabat et al. (supra). In one embodiment, for VH, the subgroup is subgroup III as described by Kabat et al. (supra).

A "human being antibody" which may also be referred to as a "human antibody," "fully human source antibody," or "fully human antibody" is an antibody whose amino acid sequence corresponds to that produced by humans or by human cells. This definition of human antibody specifically excludes humanized antibodies comprising non-human antigen-binding residues. Human antibodies can be prepared using a variety of techniques known in the art, including phage display library techniques, as described in Hoogenboom and Winter, J. Mol. Biol., 227: 381 (1991); Marks et al., J. Mol. Biol., 222: 581 (1991); Cole et al., Monoclonal Antibodies and Cancer Therapy, Alan R. Liss, p. 77 (1985); Boerner et al., J. Immunol., 147(1): 86-95 (1991). Human antibodies can be prepared by administering antigen to transgenic animals (e.g., immunized xenogeneic mice) that have been modified to produce such antibodies in response to antigenic challenge, but whose endogenous loci have been disabled (for XENOMOUSE™ technology, see, e.g., U.S. Pat. Nos. 6,075,181 and 6,150,584). For human antibodies produced via human B cell hybridoma technology, see also, e.g., Li et al., Proc. Natl. Acad. Sci. USA, 103: 3557-3562 (2006).

The term "hypervariable region" or "HVR" as used herein refers to a region of the variable domain of an antibody having a sequence hypervariable region (also referred to as "complementarity determining region" or "CDR") and/or forming a structurally defined loop ("hypervariable loop") and/or comprising an antigen-contacting residue ("antigen contact"). In general, the antibody comprises 6 HVRs (CDR regions): 3 in the VH (H1, H2, and H3) and 3 in the VL (L1, L2, and L3). Exemplary HVRs (CDR regions) herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196: 901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR (CDR region) amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR (CDR region) residues and other residues in the variable domain (e.g., FR residues) are numbered herein according to Kabat et al. (supra).

The term "variable region" or "variable domain" refers to the antibody heavy or light chain domain involved in binding an antibody to an antigen. The variable domains of the heavy and light chains (VH and VL, respectively) of natural antibodies generally have similar structures, with each domain comprising 4 conserved framework regions (FRs) and 3 complementarity determining regions (CDR regions). (See, e.g., Kindt et al., Kuby Immunology, 6th ed.) A single VH or VL domain may be sufficient to confer antigen-binding specificity.

An "antibody fragment" refers to a molecule other than an intact antibody that comprises a portion of an intact antibody that binds the antigen to which the intact antibody binds. Examples of antibody fragments include, but are not limited to, Fv, Fab, Fab', Fab'-SH, F(ab')2; diabodies; linear antibodies; single-chain antibody molecules (e.g., scFv); and multispecific antibodies formed from antibody fragments.

The term "cytotoxic agent" as used herein refers to a substance that inhibits or prevents cell function and/or causes cell death or destruction. Cytotoxic agents include, but are not limited to, radioisotopes (e.g., radioisotopes of At211, I131, I125, Y90, Re186, Re188, Sm153, Bi212, P32, Pb212, and Lu); chemotherapeutic agents or drugs (e.g., methotrexate, adriamicin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof, such as nucleolytic enzymes; antibiotics; toxins, such as small molecule toxins or enzymatically active toxins of bacterial, fungal, plant or animal origin, including fragments and/or variants thereof; various antitumor drugs or anticancer agents known in the art.

An "immunoconjugate" is a conjugate of an antibody and one or more heterologous molecules, including but not limited to cytotoxic agents.

A stimulator of interferon genes (STING) receptor agonist is a molecule that activates the STING-dependent signaling pathway to promote the secretion of type I interferon and the expression of proteins related to anti-viral and anti-tumor immunity, block virus replication, and promote the immune response to cancer cells. Such molecules are STING agonists of structural classes such as cyclic dinucleotides, aminobenzimidazoles, xanthones, acridinones, benzothiophenes and benzodioxoles.

A "subject" or "individual" is a mammal. Mammals include, but are not limited to, domesticated animals (e.g., cows, sheep, cats, dogs, and horses), primates (e.g., humans and non-human primates, such as monkeys), rabbits, and rodents (e.g., mice and rats). In certain embodiments, the subject or individual is a human.

The term "package insert" is used to refer to instructions typically included in commercial packages of therapeutic products, which comprise information on indications, usage, dosage, administration, combination therapies, contraindications and/or warnings regarding the use of such therapeutic products.

"Affinity" refers to the strength of the sum of non-covalent interactions between a single binding site of a molecule (e.g., an antibody) and its binding partner (e.g., an antigen). Unless otherwise indicated, as used herein, "binding affinity" refers to intrinsic binding affinity, which reflects a 1:1 interaction between binding partner members (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described below.

"Percent (%) amino acid sequence homology" with respect to a reference polypeptide sequence is defined as the percentage of amino acid residues in a candidate sequence that are identical with the amino acid residues in the reference polypeptide sequence, after aligning the candidate sequence with the reference polypeptide sequence and introducing gaps if necessary to achieve maximum percent sequence homology and in the event that any conservative substitutions are not considered part of the sequence homology. Determination of percent amino acid sequence homology can be accomplished in a variety of ways in the art, for example, homology alignment can be performed using software such as BLAST, BLAST-2, ALIGN or Megalign (DNASTAR®). Those skilled in the art can determine suitable parameters for aligning sequences, including any algorithms required to achieve maximal alignment over the full length of the sequences being compared.

For example, in the case of amino acid sequence comparison using ALIGN-2, the % amino acid sequence homology of a given amino acid sequence A to, with, or relative to a given amino acid sequence B is calculated as follows:

$$100\times\text{fraction } X/Y$$

where X is the number of amino acid residues scored as identical matches by the sequence alignment program ALIGN-2 when the program aligns A with B, and where Y is the total number of amino acid residues in B. It will be understood that where the length of amino acid sequence A is not equal to the length of amino acid sequence B, the % amino acid sequence homology of A to B will not equal to the % amino acid sequence homology of B to A. All % amino acid sequence homology values used herein are obtained using the ALIGN-2 computer program unless otherwise indicated.

2. Antibody, Preparation Method, Composition and Article

1) Antibody

The present application relates to anti-CLDN18.2 antibodies. In certain embodiments, the present application provides an anti-CLDN18.2 antibody comprising at least 1, 2, 3, 4, 5 or 6 following hypervariable regions (HVRs) or binding domains referred to as complementarity determining regions (CDRs): (a) HVR-H1 comprising the amino acid sequence of the sequence SEQ ID NO:18 or SEQ ID NO:21, or an amino acid sequence having a homology of at least 90%, 95%, 96%, 97%, 98%, 99% to the sequence; (b) HVR-H2 comprising the amino acid sequence of sequence SEQ ID NO:19 or SEQ ID NO:22, or an amino acid sequence having a homology of at least 90%, 95%, 96%, 97%, 98%, 99% to the sequence; (c) HVR-H3 comprising the amino acid sequence of the sequence SEQ ID NO:20 or SEQ ID NO:23, or an amino acid sequence having a homology of at least 90%, 95%, 96%, 97%, 98%, 99% to the sequence; (d) HVR-L1 comprising the amino acid sequence of the sequence SEQ ID NO:24 or SEQ ID NO:27, or an amino acid sequence having a homology of at least 90%, 95%, 96%, 97%, 98%, 99% to the sequence; (e) HVR-L2 comprising the amino acid sequence of the sequence SEQ ID NO:25 or SEQ ID NO:28, or an amino acid sequence having a homology of at least 90%, 95%, 96%, 97%, 98%, 99% to the sequence; and (f) HVR-L3 comprising the amino acid sequence of SEQ ID NO:26 or SEQ ID NO:29, or an amino acid sequence having a homology of at least 90%, 95%, 96%, 97%, 98%, 99% to the sequence. In some cases, the heavy chain variable (VH) domain (region) of the anti-CLDN18.2 antibody may comprise an amino acid sequence having a homology of at least 90% (e.g., at least 91%, 92%, 93%, 94%, 95%, 96%, 97%, 98% or 99% sequence homology) to the sequence SEQ ID NO:36 or SEQ ID NO:37, or the amino acid sequence of SEQ ID NO:36 or SEQ ID NO:37, and/or its light chain variable (VL) domain (region) comprises an amino acid sequence having a homology of at least 90% (e.g., at least 91%, 92%, 93%, 94%, 95%, 96%, 97%, 98% or 99% sequence homology) to the sequence SEQ ID NO:38 or SEQ ID NO:39, or the amino acid sequence of SEQ ID NO:38 or SEQ ID NO:39.

In some embodiments, the anti-CLDN18.2 antibody comprises a heavy chain variable region and a light chain variable region, wherein the heavy chain variable region comprises the following amino acid sequence:

2) Antibody Fragment

In certain embodiments, the antibodies provided herein are antibody fragments. Antibody fragments include, but are not limited to, Fab, Fab', Fab'-SH, (Fab')2, Fv and scFv fragments and others described below. For a review of certain antibody fragments, see Hudson et al., Nat. Med. 9:129-134 (2003). For scFv fragments, see e.g., WO 93/16185.

A bifunctional antibody is an antibody fragment with two antigen-binding sites, which can be bivalent or bispecific. See e.g., EP 404,097; WO1993/01161. Trifunctional and tetrafunctional antibodies can be found in, e.g., Hudson et al., Nat. Med. 9:129-134 (2003).

A single domain antibody is an antibody fragment comprising all or part of a heavy chain variable domain or all or part of a light chain variable domain of an antibody. In certain embodiments, the single domain antibody is a human single domain antibody (see, e.g., U.S. Pat. No. 6,248,516 B1).

Antibody fragments can be produced by various techniques including, but not limited to, production by proteolytic digestion of intact antibodies and recombinant host cell (e.g., *E. coli* or phage).

3) Chimeric and Humanized Antibodies

In certain embodiments, the antibodies provided herein are chimeric antibodies. The preparation of chimeric antibodies can be found in, eg, U.S. Pat. No. 4,816,567.

In certain embodiments, the chimeric antibody is a humanized antibody. Typically, non-human antibodies are humanized to reduce immunogenicity to humans while retaining the specificity and affinity of the parental non-human antibodies. In general, humanized antibodies comprise one or more variable domains in which all HVR (CDR) regions, or portions thereof, are derived from non-human antibodies, and FRs (or portions thereof) are derived from human antibody sequences. A humanized antibody optionally comprises at least a portion of a human constant region. In some embodiments, some FR residues in a humanized antibody may be replaced with corresponding residues from a non-human antibody to repair or improve the affinity of the antibody.

For humanized antibodies and production methods thereof, see U.S. Pat. Nos. 5,821,337, 7,527,791, 6,982,321 and 7,087,409.

4) Human Antibody

In certain embodiments, the antibodies provided herein are human antibodies. Human antibodies can be produced using various techniques known in the art.

Whole human antibodies or whole antibodies with human variable regions can be prepared by administering an immunogen to a modified transgenic animal, followed by challenge with the antigen. Such animals typically comprise all or part of the human immunoglobulin loci which replace the endogenous immunoglobulin loci or are present extrachromosomally or randomly integrated into the animal's chromosomes. In such transgenic mice, the endogenous immunoglobulin loci are generally inactivated. For methods of obtaining human antibodies from transgenic animals, see, e.g., U.S. Pat. Nos. 6,075,181 and 6,150,584 (describing XENOMOUSE™ technology); U.S. Pat. Nos. 5,770,429; 7,041,870 (describing K-M technology); and US application publication No. 2007/0061900. Human variable regions derived from intact antibodies produced by such animals can be further modified, e.g., by combining them with different human constant regions.

Human antibodies can also be made by hybridoma-based methods. Human myeloma and mouse-human hybrid myeloma cell strains for the production of human monoclonal antibodies have been described, see e.g., Boemer et al., J. Immunol., 147:86 (1991). Human antibodies produced via human B cell hybridoma technology are also described in Li et al., Proc. Natl. Acad. Sci. USA, 103: 3557-3562 (2006). Other methods include, e.g., those described in U.S. Pat. No. 7,189,826 (describing production of monoclonal human IgM antibodies from hybridoma cell strains) and Ni, Xiandai Mianyixue, 26(4):265-268 (2006) (describing human-human hybridomas).

Human antibodies can also be prepared by isolating Fv clone variable domain sequences selected from phage display libraries of human source. Such variable domain sequences can then be combined with the desired human constant domains.

Specifically, antibodies of the application with high affinity can be isolated by screening combinatorial libraries for antibodies with binding activity to CLDN18.2. For example, various methods are known in the art for generating phage display libraries and screening such libraries for antibodies with desired binding characteristics. Such methods can be found, for example, in Hoogenboom et al., Methods in Molecular Biology 178:1-37 (O'Brien et al., eds., Human Press, Totowa, NJ, 2001), Marks and Bradbury, Methods in Molecular Biology 248:161-175 (Edited by Lo, Human Press, Totowa, NJ, 2003) and Lee et al., J. Immunol. Methods 284(1-2):119-132 (2004).

In some phage display methods, the VH and VL gene lineages are individually cloned by polymerase chain reaction (PCR) and randomly recombined in a phage library, followed by screening against antigen-binding phage. Phages typically present antibody fragments as single-chain Fv (scFv) fragments or Fab fragments. Patents describing human antibody phage libraries include, for example: U.S.

Pat. No. 5,750,373 and US Patent Publication Nos. 2005/0079574, 2005/0119455, 2005/0266000, 2007/0117126, 2007/0237764, 2007/0292936 and 2009/0002360.

Antibodies or antibody fragments isolated from human antibody libraries are considered herein to be human antibodies or human antibody fragments.

5) Multispecific Antibody

In any of the above aspects, the anti-CLDN18.2 antibodies provided herein are multispecific antibodies, e.g., bispecific antibodies. Multispecific antibodies are monoclonal antibodies that have binding specificities for at least two different sites. In certain embodiments, one binding specificity is for CLDN18.2 and the other binding specificity is for any other antigen (e.g., a second biomolecule, e.g., a cell surface antigen, e.g., a tumor antigen). Accordingly, bispecific anti-CLDN18.2 antibodies can have binding specificity for CLDN18.2 and tumor antigens such as CD3, CD20, FcRH5, HER2, LYPD1, LY6G6D, PMEL17, LY6E, CD19, CD33, CD22, CD79A, CD79B, EDAR, GFRA1, MRP4, RET, Steap1 or TenB2. Bispecific antibodies can be prepared as full-length antibodies or antibody fragments.

Techniques for making multispecific antibodies include, but are not limited to, recombinant co-expression of two immunoglobulin heavy chain-light chain pairs with different specificities, see WO 93/08829, WO2009/08025, and WO 2009/089004A1 etc.

6) Antibody Variants

The antibodies of the present application encompass amino acid sequence variants of the anti-CLDN18.2 antibodies of the present application. For example, antibody variants prepared to further improve the binding affinity and/or other biological properties of the antibody may be desired.

Amino acid sequence variants of an antibody can be prepared by introducing appropriate modifications into the nucleotide sequence encoding the antibody. Such modifications include, for example, deletions and/or insertions and/or substitutions of residues within the amino acid sequence of the antibody. Any combination of deletions, insertions and substitutions can be made to obtain the final construct, provided that the final construct has the desired characteristics, such as the binding property to the CLDN18.2 antigen.

In certain embodiments, antibody variants with one or more amino acid substitutions are provided. Substitution mutants (including conservative substitution mutants or non-conservative substitution mutants) can be obtained by substitution at one or more sites in the HVR (CDR) region and/or FR region.

Amino acids can be grouped according to common side chain properties:

(1) Hydrophobic: Norleucine, Met, Ala, Val, Leu, Ile;
(2) Uncharged and hydrophilic: Cys, Ser, Thr, Asn, Gln;
(3) Acidic: Asp, Glu;
(4) Basic: His, Lys, Arg;
(5) Residues affecting chain orientation: Gly, Pro;
(6) Aromatic: Trp, Tyr, Phe.

Conservative substitutions are defined as substitutions between the same group of amino acids, and non-conservative substitutions are defined as substitutions of amino acids from one of the different classes by amino acids from another class. Antibody variants of the application can be obtained by introducing amino acid substitutions into the antibodies of the application and screening the product for the desired activity (e.g., retention/improvement of antigen binding or improvement of ADCC or CDC).

The present application encompasses antibody variants obtained according to the antibodies disclosed herein that comprise non-conservative mutations and/or conservative mutations, so long as the variants still possess the desired CLDN18.2 binding activity.

One type of substitutional variants involves antibody variants that substitute one or more hypervariable region residues of a parent antibody (e.g., a humanized or human antibody). In general, the resulting variant selected for further study will be modified (e.g., improved) relative to the parent antibody with respect to certain biological properties (e.g., increased affinity) and/or will substantially retain certain biological properties of the parent antibody. Exemplary substitutional variants are affinity matured antibodies, which can be conveniently produced using, for example, phage display-based affinity maturation techniques such as those described herein. Briefly, one or more HVR (CDR) residues are mutated and the mutated antibody is displayed on phage, and the mutated antibody is screened for a particular biological activity (e.g., binding affinity).

In certain embodiments, substitutions, insertions or deletions may occur within one or more of the HVRs (CDRs), so long as such changes do not substantially impair the ability of the antibody to bind CLDN18.2. For example, conservative changes can be made in the HVR (CDR) that do not substantially reduce binding affinity. For example, such changes may be outside the antigen-contacting residues in the HVR, e.g., conservative or non-conservative amino acid substitutions may occur at one 1, 2, 3, 4, 5 amino acid residues of the FR region.

7) Recombination Method

Anti-CLDN18.2 antibodies of the application can be prepared using recombinant methods, e.g., as described in U.S. Pat. No. 4,816,567. In one embodiment, an isolated nucleic acid encoding the anti-CLDN18.2 antibody described herein is provided. Such nucleic acids may encode the VL amino acid sequence and/or the VH amino acid sequence of the antibody. In another embodiment, one or more vectors (e.g., expression vectors) comprising such nucleic acids are provided. In another embodiment, host cells comprising such nucleic acids are provided. In one such embodiment, the host cell comprises (e.g., transformed to have): (1) a vector comprising a nucleic acid encoding an amino acid sequence comprising the VL of the antibody and an amino acid sequence comprising the VH of the antibody; or (2) a first vector comprising a nucleic acid encoding an amino acid sequence comprising the VL of the antibody and a second vector comprising a nucleic acid encoding an amino acid sequence comprising the VH of the antibody. In one embodiment, the host cell is a eukaryotic cell, such as a Chinese hamster ovary (CHO) cell or a lymphoid cell (e.g., Y0, NSO, Sp20 cells). In one embodiment, a method for making an anti-CLDN18.2 antibody is provided, wherein the method comprises culturing a host cell comprising a nucleic acid encoding the antibody as provided above under conditions suitable for expression of the antibody, and optionally recovering the antibody from the host cell (or host cell culture medium).

For recombinant production of anti-CLDN18.2 antibodies, nucleic acids encoding the antibody are isolated (e.g., as described above) and inserted into one or more vectors for further cloning and/or expression in host cells. Such nucleic acids can be readily isolated and sequenced using conventional procedures (e.g., by using oligonucleotide probes capable of specifically binding to the genes encoding the heavy and light chains of the antibody).

Suitable host cells for cloning or expressing antibody-encoding vectors include prokaryotic or eukaryotic cells as described herein. For example, antibodies can be produced in bacteria, especially when glycosylation and Fc effector functions are not required. For expression of antibody fragments and polypeptides in bacteria, see, e.g., U.S. Pat. Nos. 5,648,237, 5,789,199, and 5,840,523. Following expression, the antibody in the soluble fraction can be isolated from the bacterial cytoplasm and can be further purified.

In addition to prokaryotes, eukaryotic microorganisms such as filamentous fungi or yeast are also suitable cloning or expression hosts for antibody-encoding vectors, including fungal and yeast strains of which glycosylation pathways have been "humanized" to produce antibodies with partially or fully human glycosylation patterns. See Li et al., Nat. Biotech. 24: 210-215 (2006).

Host cells suitable for expression of glycosylated antibodies can also be derived from multicellular organisms (invertebrates and vertebrates). Examples of invertebrate cells include plant and insect cells. A number of baculovirus strains have been identified to be used for binding to insect cells, especially for transfection of *Spodoptera frugiperda* cells.

Plant cell cultures can also be used as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells can also be used as hosts. For example, mammalian cell lines suitable for growth in suspension may be suitable. Other examples of suitable mammalian host cell strains are SV40-transformed monkey kidney CV1 cell strains (COS-7); human embryonic kidney cell strains (e.g., 293 cells); baby hamster kidney cells (BHK); mouse sertoli cells (e.g., TM4 cells); monkey kidney cells (CV1); African green monkey kidney cells (VERO-76); human cervical carcinoma cells (HELA); canine kidney cells (MDCK); buffalo rat hepatocytes (BRL3A); human lung cells (W138); human hepatocytes (Hep G2); mouse breast tumors (MMT 060562); TRI cells; MRC 5 cells; Chinese hamster ovary (CHO) cells, including DHFR-CHO cells; and myeloma cell strains such as Y0, NS0 and Sp2/0.

8) Immunoconjugate

The present application also provides immunoconjugates comprising the anti-CLDN18.2 antibody herein in combination with one or more cytotoxic agents, such as chemotherapeutic or chemotherapeutic drugs, growth inhibitors, toxins (for example, protein toxins, enzymatically active toxins of bacterial, fungal, plant or animal origin or fragments thereof) or radioisotopes.

In one embodiment, the immunoconjugate is an antibody-drug conjugate (ADC), wherein the antibody is conjugated to one or more drugs, including but not limited to maytansine, orlistatin, dolastatin, methotrexate, vindesine, taxane, trichothecene and CC1065.

In another embodiment, the immunoconjugate comprises a conjugate of the anti-CLDN18.2 antibody as described herein with an enzymatically active toxin, or a fragment thereof, including but not limited to diphtheria A chain, non-binding active fragments of diphtheria toxin, exotoxin A chain and trichothecene, etc.

In another embodiment, the immunoconjugate comprises a radio-conjugate formed by combining an anti-CLDN18.2 antibody as described herein with a radioactive atom. A variety of radioisotopes can be used to generate radio-conjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$, and radioisotopes of Lu.

Conjugates of antibodies and cytotoxic agents can be made using a variety of bifunctional protein coupling agents, such as N-succinimidyl-3-(2-pyridyldithio)propionate (SPDP), succinimido-4-(N-maleimidomethyl)cyclohexane-1-carboxylate (SMCC), imidothiacyclopentane (IT), bifunctional derivatives of imidate ester (such as dimethyl adipate hydrochloride), active esters (such as disuccinimide octanedioate), aldehydes (such as glutaraldehyde), diazido compounds (such as bis (p-azidobenzoyl) hexanediamine), disazo derivatives (such as bis(p-diazobenzoyl) ethanediamine), diisocyanates (such as toluene 2,6-diisocyanate) and double active fluorine compounds (such as 1,5-difluoro-2, 4-dinitrobenzene).

9) Pharmaceutical Preparation

A pharmaceutical preparation of the anti-CLDN18.2 antibody herein is prepared by mixing the antibodies of the desired purity with one or more optional pharmaceutically acceptable carriers in the form of a lyophilized formulation or an aqueous solution. Pharmaceutically acceptable carriers are generally non-toxic to the acceptor at the dosages and concentrations employed, and include, but are not limited to: buffers, such as phosphates, citrates, and other organic acids; antioxidants, including ascorbic acid and methionine; preservatives (such as octadecyldimethylbenzyl ammonium chloride; hexahydrocarbon quaternary ammonium chloride; benzalkonium chloride; benzethonium chloride; phenol, butanol or benzyl alcohol; alkyl ethyl p-hydroxybenzoate such as methyl ethyl p-hydroxybenzoate or propyl ethyl p-hydroxybenzoate; catechol; resorcinol; cyclohexanol; 3-pentanol; and m-cresol); low molecular weight (less than about 10 residues) polypeptides; proteins such as serum albumin, gelatin or immunoglobulins; hydrophilic polymers such as polyvinylpyrrolidone; amino acids such as glycine, glutamic acid, asparagine, histidine, arginine or lysine; monosaccharides, disaccharides and other carbohydrates including glucose, mannose or dextrin; chelating agents such as EDTA; sugars such as sucrose, mannitol, fucose or sorbitol; salt-forming counterions, such as sodium; metal complexes (e.g., zinc-protein complexes); and/or nonionic surfactants, such as polyethylene glycol (PEG).

Exemplary lyophilized antibody formulations are described in U.S. Pat. No. 6,267,958. Aqueous antibody formulations include those described in U.S. Pat. No. 6,171,586 and WO2006/044908.

The preparation herein may also comprise more than one active ingredient as necessary for the particular indication being treated, preferably active ingredients having complementary activities that do not adversely affect each other. For example, it may be desirable to further provide additional therapeutic agents (e.g., chemotherapeutic agents, cytotoxic agents, growth inhibitors, and/or antihormone agents). Such active ingredients are suitably present in combination in amounts effective for the intended purpose.

10) Articles

In another aspect of the application, an article comprising the antibody or pharmaceutical composition of the application is provided. The article comprises a container and a label or package insert on or associated with the container. Suitable containers include, for example, bottles, vials, syringes, IV solution bags, and the like. Such containers may be formed from various materials, such as glass or plastic. The container holds the composition of the present application itself or in combination with another composition, and may have a sterile access port (e.g., the container may be an intravenous solution bag or a vial having a stopper which can be pierced by a hypodermic needle). At least one active agent in the composition is the antibody of the application.

The label or package insert indicates that the composition is used to treat the selected tumor. Furthermore, the article can comprise (a) a first container comprising a composition therein, wherein the composition comprises an antibody of the application; and (b) a second container comprising a composition therein, wherein the composition comprises another tumor treatment drug or another antibody. The article in this embodiment of the application may further comprise a package insert indicating that such compositions can be used to treat tumors. Alternatively, or in addition, the article may further comprise a second (or third) container comprising a pharmaceutically acceptable buffer, such as bacteriostatic water for injection (BWFI), phosphate buffered saline, Ringer's solution and dextrose solution. It may further include other materials as may be desirable from a commercial and user standpoint, including other buffers, diluents, filters, needles and syringes.

11) Detection Reagents and Kits

The present application also provides cancer detection reagents comprising the anti-CLDN18.2 antibody or antigen-binding fragments thereof herein. Cancer detection reagents can be used to test tumor or blood tissue from actual patients. For example, testing can be performed using PCR, microarray or chip technology. Once cancer detection reagents are found to be present in a patient, those reagents can be selected for use in treating the patient or directing therapy.

In one embodiment, the anti-CLDN18.2 antibody or antigen-binding fragment thereof is chemically labeled, specifically, enzymatic labels such as alkaline phosphatase and glucose oxidase; fluorescent labels such as fluorescein and rhodamine; isotopes labels such as iodine (125I, 131I), carbon (14C), sulfur (35S), tritium (3H), indium (121In), and technetium (99mTc); or chemiluminescent labels such as luminol and fluorescein enzymes.

The present application also provides a cancer detection kit comprising the anti-CLDN18.2 antibody or antigen-binding fragment thereof herein. The kit may also comprise a labeled anti-CLDN18.2 antibody or antigen-binding fragment thereof. Specifically, the cancer detection kit can be used to detect gastric cancer, pancreatic cancer or esophageal cancer.

Specific embodiments of the present application will be described in more detail below with reference to the accompanying drawings. While specific embodiments of the present application are shown in the drawings, it should be understood that the present application may be embodied in various forms and should not be limited by the embodiments set forth herein. Rather, these embodiments are provided such that the present application will be more thoroughly understood, and will fully convey the scope of the present application to those skilled in the art.

EXAMPLE

Example 1 Preparation of Materials for Immunization and Screening (1) Construction of Human hCLDN18.2-TCE (T-Cell Epitope Peptide) Retrovirus Expression Plasmid The hCLDN18.2 cDNA (SEQ ID NO:1) was cloned and fused with the T-cell epitope peptide at the C-terminal, resulting in hCLDN18.2-TCE. T-cell epitope peptides can make antigens break through immune tolerance and promote antibody production (Percival-Alwyn J. et al, mAbs, 2015, 7(1), 129-137). The hCLDN18.2-TCE was cloned into a retroviral vector to obtain the hCLDN18.2-TCE retroviral expression plasmid. The hCLDN18.2-TCE retrovirus expression plasmid was transiently transfected into HEK293-T cells, and the expression of hCLDN18.2 on the surface of HEK293-T cells was analyzed by flow cytometry 72 hours after transfection. The primary antibody (1st Ab) was the home-made positive control (Benchmarker) chimeric antibody 163E12. Cells were first incubated with the primary antibody (1 μg/mL) at 4° C. for 45 min, washed with PBS, and then incubated with Alexa Fluor© 488-labeled goat anti-human Fc secondary antibody (Thermofisher®, Cat. No. A-11013)) (2nd Ab, 1:200 dilution) at 4° C. for 45 minutes. Flow cytometry (FACS) analysis was performed after washing twice with PBS, and the negative control cells were incubated with secondary antibody only. The results were shown in FIG. 1, showing that there was no hCLDN18.2 expression on the surface of wild HEK293-T cells; 80.9% of HEK293-T cells transiently transfected with hCLDN18.2-TCE retrovirus expression plasmid (HEK293T CLDN18.2 TCE) were positive cells expressing hCLDN18.2. This vector plasmid will be used in (1) DNA immunization scheme in Example 2.

(2) Mouse Tumor Cells Expressing High Levels of hCLDN18.2-TCE

Figure 2:
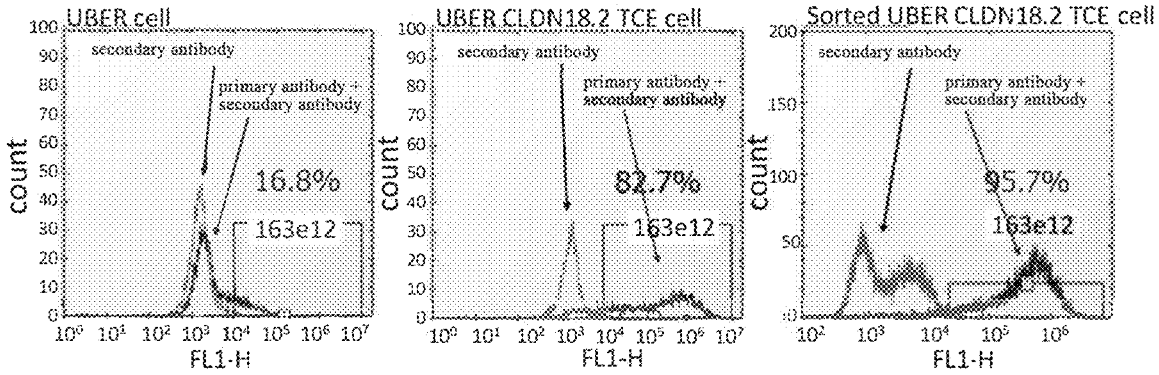
FIG. 2. Transfection of mouse tumor cell lines with hCLDN18.2-TCE lentiviral particles and sorting of mouse tumor cells expressing high levels of hCLDN18.2-TCE by flow cytometry.

The hCLDN18.2-TCE retrovirus expression plasmid was mixed with the lentiviral packaging plasmid and transfected into 293-T cells to prepare hCLDN18.2-TCE lentiviral particles. The hCLDN18.2-TCE lentiviral particles were transfected into mouse tumor cell lines, and 72 hours later, flow cytometry was performed and the mouse tumor cells pool with high expression of hCLDN18.2-TCE were detected and sorted. The primary antibody (1st Ab) was the home-made positive control (Benchmarker) chimeric antibody 163E12. Cells were first incubated with the primary antibody (1 μg/mL) at 4° C. for 45 minutes, washed with PBS and then incubated with Alexa Fluor© 488-labeled goat anti-human Fc secondary antibody (2nd Ab, 1:200 dilution) at 4° C. for 45 minutes. Flow cytometry (FACS) analysis was performed after washing twice with PBS, and the negative control cells were incubated with the secondary antibody only. The results were shown in FIG. 2, showing that only 16.8% of the wild-type mouse tumor cells (UBER parental) had positive signals on the surface and hCLDN18.2-TCE retrovirus-transfected mouse tumor cells (UBER CLDN18.2 TCE) had 82.7% positive cells. After sorting by flow cytometry analysis, up to 95.7% of mouse tumor cells had high levels of hCLDN18.2-TCE expression. The mouse tumor cells of hCLDN18.2-TCE will be used in (2) cellular immunization scheme in Example 2.

(3) Preparation of hCLDN18.2 Extracellular Loop 1 Virus-Like Particles

According to the method published by Thorsten K. (Thorsten K., et al, Cancer Res, 2011, 71(2), 515-527), extracellular loop1 (ECL1) (SEQ ID NO:2) of hCLDN18.2 was inserted into the major immunodominant region (MIR) of Hepatitis B virus core antigen (HBcAg), and a G4SG4 linker was introduced at the N-terminal and C-terminal of ECL1, and a 6×His tag was added to the C-terminal of the full-length fusion protein. The full-length gene of the fusion protein was synthesized, cloned into pET24a (+) plasmid, and then transfected into the BL21(DE3) *E. coli* expression system for the expression of the fusion protein. After purification of the fusion protein, HBV hCLDN18.2 extracellular loop 1 virus-like particles were prepared in renaturation buffer. The preparation of the extracellular loop 1 virus-like particles of hCLDN18.2 will be used in (3) virus-like particle multiple-point repetitive immunization-cellular immunization scheme and (4) virus-like particle tarsus joint immunization-cellular immunization scheme in Example 2.

(4) Construction of CLDN18 Stably Transfected Cell Strain

Figure 3:
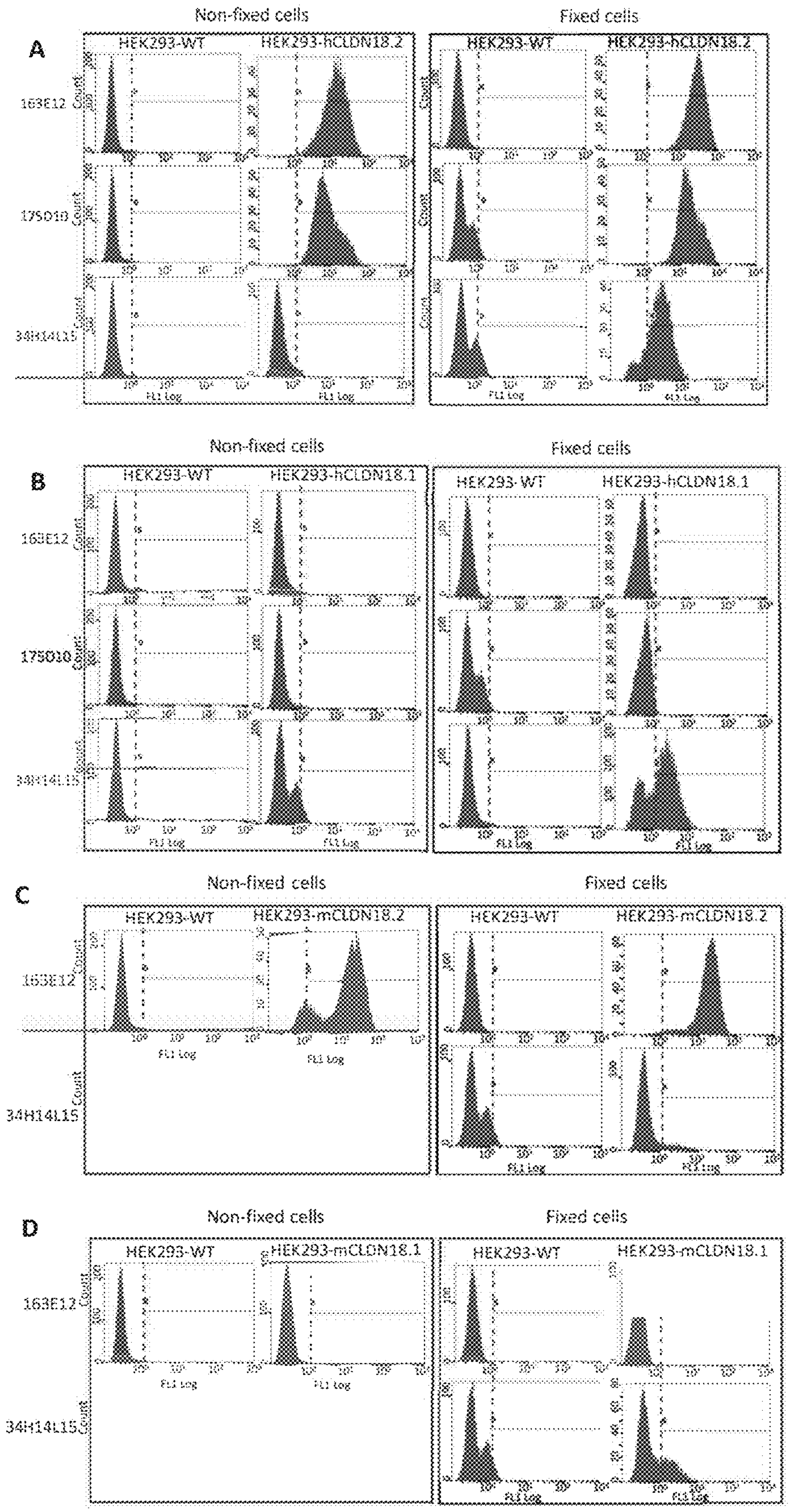
FIG. 3. Flow cytometric analysis of hCLDN18.2, hCLDN18.1, mCLDN18.2, and mCLDN18.1 stably transfected cell lines.

Full length hCLDN18.2 (SEQ ID NO:4), hCLDN18.1 (SEQ ID NO:5), mouse mhCLDN18.2 (SEQ ID NO:6), and mCLDN18.1 (SEQ ID NO:7) genes were synthesized respectively, and cloned into pcDNA3.4 vector plasmid respectively. Plasmids were transfected into HEK293 cells and neomycin (G418) was added for pressure selection. The Stably transfected HEK293 cell strains with high expression of hCLDN18.2, hCLDN18.1, m hCLDN18.2 and mCLDN18.1 were selected by limited dilution method. The test results of flow cytometry showed that the Stably transfected HEK293 cell strains (HEK293-hCLDN18.2, HEK293-mCLDN18.2) transfected with hCLDN18.2 and mCLDN18.2, both paraformaldehyde-fixed and non-fixed cells can be specifically recognized by home-made anti-CLDN18.2 positive control antibody 163E12 or 175D10 (FIG. 3. A, C), and can also be recognized by the commercial broad spectrum anti-CLDN18 antibody 34H14L15 (Abcam® catalog number ab203563) (FIG. 3. A, C). Stably transfected HEK293 cell strains transfected with hCLDN18.1 and mCLDN18.1 (HEK293-hCLDN18.1, HEK293-mCLDN18.1), both paraformaldehyde-fixed and non-fixed cells cannot be specifically recognized by home-made anti-CLDN18.2 positive control antibody 163E12 or 175D10 (FIG. 3. B, D), but can be recognized by the commercial broad spectrum anti-CLDN18 antibody (34H14L15) (FIG. 3. B, D). The above Stably transfected HEK293 cell strains will be used for hybridoma screening in Example 3.

(5) Preparation of Positive Control Antibodies 43A11, 175D10 and 163E12

Figure 4:
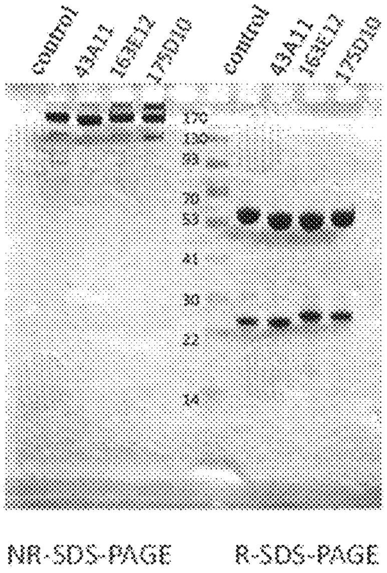
FIG. 4. SDS-PAGE detection of the positive control antibodies 43A11, 175D10 and 163E12.

Human-mouse chimeric positive control antibodies 43A11 heavy chain (SEQ ID NO:8) and light chain (SEQ ID NO:9), 175D10 heavy chain (SEQ ID NO: 10) and light chain (SEQ ID NO:11), 163E12 heavy chain (SEQ ID NO:12) and light chain (SEQ ID NO:13) full-length genes were synthesized respectively, with signal peptides added at the N-terminal respectively, and then cloned into pcDNA3.4 eukaryotic expression vector. The 43A11, 175D10 and 163E12 heavy chain and light chain expression plasmids were mixed and co-transfected into CHOS cells for transient protein expression. The supernatant was collected, affinity purified with Protein A and detected by SDS-PAGE. The results were shown in FIG. 4.

Example 2 Mouse Immunization Program and Hybridoma Preparation

A total of 4 immunization schemes were adopted (Table 1), and at least two different strains of mice were used for each immunization scheme (Table 2). In each immunization scheme, some individual mice showed higher levels of serum immune titers. Mice individuals with high levels of immune titers in each immunization scheme were sacrificed and their spleens were removed. B lymphocytes were isolated, mixed, and then electrofused with cells from mouse myeloma cell lines to prepare hybridomas. A total of three batches of hybridoma preparation were prepared (Table 2).

TABLE 1

| Number | Immunization scheme | Immunization material | Mice strain and number | Immunization method and immune titer detection |
|---|---|---|---|---|
| 1 | DNA immunization scheme | CLDN18.2-TCE viral expression vector | NZB/W(M1, M2) BALC/c(M3, M4) | The CLDN18.2-TCE virus expression plasmid was injected through the tail vein for primary immunization (Zhang G F, et al. Human Gene Ther. 1999, 10, 1735-1737; Liu F, et al. Gene Ther. 1999, 6, 1258-1266), and the immune titer of the mouse serum was detected by flow cytometry three weeks after the immunization. The mice with serum reaction were boosted with HEK293 cells expressing high levels of human CLDN18.2 (Sotoshi N, et al. J Immunol Method, 2003, 280, 59-72). One week after booster immunization, flow cytometry was used to detect the immune titer of mouse serum. Mice with high immune titers were selected to be sacrificed and spleen B cells were fused to prepare hybridomas. |
| 2 | Cellular immunization scheme | Mouse tumor cell line expressing high levels of CLDN18.2-TCE | NZB/W(M1, M2, M3, M4) BALB/c(M1, M2, M3, M4) | Mice were subcutaneously inoculated with mouse tumor cell lines expressing high levels of CLDN18.2-TCE, and the immune titer of mouse serum was detected by flow cytometry in the second and fourth weeks. The mice with serum reaction and insignificant tumor growth were boosted at week 5 with mouse tumor cell lines expressing CLDN18.2-TCE (Sotoshi N, et al. J Immunol Method, 2003, 280, 59-72). And three days after booster immunization, mice with high immune titers were selected to be sacrificed and the spleen B cells were fused to prepare hybridomas. |
| 3 | Virus-like particle multiple-point repeat immunization-cellular immunization scheme | Virus-like particles fused to express extracellular loop 1 of CLDN18.2 | NZB/W(M1, M2) B6;129(M3, M4) | Virus-like particles fused to express extracellular loop 1 of CLDN18.2 were first immunized by multiple-point repeat immunization method (Edward AG, Antibodies: A laboratory manual (Second Edition), 2012, Chapter 6, Protocol 30), and the immune titer of mouse serum against virus-like particles was detected by ELISA method one week later. The mice with high immune titer were selected for further immunization with the |

TABLE 1-continued

| Number | Immunization scheme | Immunization material | Mice strain and number | Immunization method and immune titer detection |
|---|---|---|---|---|
| | | | | mouse tumor cell line with CLDN18.2-TCE, and the immune titer of the mouse serum was detected by flow cytometry at the fourth week after cell immunization. The mice with serum reaction were boosted with cells (Sotoshi N, et al. J Immunol Method, 2003, 280, 59-72), and three days later, the mice were sacrificed and spleen B cells were fused to prepare hybridomas. |
| 4 | Virus-like particle tarsus joint immunization-cellular immunization scheme | Virus-like particles fused to express extracellular loop 1 of CLDN18.2 | NZB/W(M1, M2) B6;129(M3, M4) SJL(M5, M6, M7) BALB/c(M8, M9, M10, M11) | Virus-like particles fused to express extracellular loop 1 of CLDN18.2 were preliminarily immunized by tarsus joint immunization method (Edward AG, Antibodies: A laboratory manual (Second Edition), 2012, Chapter 6, Protocol 18), and the immune titer of mouse serum against virus-like particles was detected by ELISA method one week later. The mice with high immune titer were selected for further immunization with the mouse tumor cell line with CLDN18.2-TCE, and the immune titer of the mouse serum was detected by flow cytometry at the fourth week after cell immunization. The mice with serum reaction were boosted with cells (Sotoshi N, et al. J Immunol Method, 2003, 280, 59-72), and three days later, the mice were sacrificed and spleen B cells were fused to prepare hybridomas. |

TABLE 2

| Mouse hybridoma preparation batch | Batch 1 | Batch 2 | Batch 3 |
|---|---|---|---|
| Source of mice with a high immune titer | DNA immunization scheme: BALB/c mouse M3, M4 | Virus-like particle multiple-point repeat immunization-cellular immunization scheme: NZB/W mouse M1, M2, B6; 129 mouse M3; Virus-like particle tarsus joint immunization-cellular immunization scheme: B6;129 mouse M4, SJL mouse M6, BALB/c mouse M9 | Cellular immunization scheme: NZB/W mouse M3 ; Virus-like particle multiple-point repeat immunization-cellular immunization scheme: B6; 129 mouse M4; Virus-like particle tarsus joint immunization-cellular immunization scheme: B6; 129 mouse M3 |

Example 3 Hybridoma Screening

The hybridomas from three batches were cloned and cultured by limited dilution method, and the supernatant of the clone was used for three rounds of binding or reverse binding screening by flow cytometry, antibody typing and antibody-dependent cytotoxicity (ADCC) assay. A total of 128 hybridoma clones with ADCC function were screened out, which can specifically bind strongly to CLDN18.2 but not or weakly bind to CLDN18.1. The screening steps and the hybridoma clones obtained by screening at each stage were summarized in Table 3.

TABLE 3

| Mouse hybridoma batch | Batch 1 | Batch 2 | Batch 3 |
|---|---|---|---|
| Cloning by limited dilution | 10 384-well plates (plates 1-10), 0.8 cells/well | 10 384-well plates (plates 11-20), 4.8 cells/well (plates 11-15) and 3.4 cells/well (plates 16-20) | 10 384-well plates (plates 21-30), 1.3 cells/well |
| After 2 weeks of culture, the supernatant from the 384-well plate was taken for primary screening | | | |
| Primary screening | 341 positive clones (they were amplified, | 336 positive clones, MFI > 75,000 (plates | 89 positive clones, MFI > 90,000 |

TABLE 3-continued

| Mouse hybridoma batch | Batch 1 | Batch 2 | Batch 3 |
|---|---|---|---|
| | and cryopreserved, and the saturated supernatant was collected), MFI > 100,000 | 11-15), MFI > 80,000 (plates 16-20) | |
| Confirmation screening | 165 positive clones, HEK293-hCLDN18.2 MFI > 200,000, and HEK293-hCLDN18.1 MFI < 100,000. (They were amplified, and cryopreserved, and the saturated supernatant was collected) | 120 positive clones, HEK293-hCLDN18.2 MFI > 50,000, and HEK293-hCLDN18.1 MFI < 40,000. (They were amplified, and cryopreserved, and the saturated supernatant was collected) | 21 positive clones, HEK293-hCLDN18.2 MFI > 70,000, and HEK293-hCLDN18.1 MFI < 30,000. (They were amplified, and cryopreserved, and the saturated supernatant was collected) |
| Verification screening | The supernatant of 306 positive clones derived from three confirmation screens were subjected to verification screening in 5 engineered cell lines (HEK293-hCLDN18.2 cells, HEK293-hCLDN18.1 cells, HEK293-mCLDN18.2 cells, HEK293-mCLDN18.1 cells and HEK293 wild-type cells) | | |
| Antibody typing | The supernatant of 306 positive clones derived from the three confirmation screens were subjected to antibody subtyping detection | | |
| Antibody -dependent cytotoxicity detection | Based on the results of the aforementioned experimental methods, the saturated supernatant of 128 positive clones were selected for antibody-dependent cytotoxicity detection. | | |
| The supernatant of 128 positive clones was subjected to immunohistochemistry (IHC) detection on FFPE tissue sections | | | |

1) Primary screening: binding of the expression product in the supernatant of each clone to a mouse tumor cell line expressing high levels of CLDNT8.2-TCF (UBER CLDNT8.2 TCF) was analyzed by flow cytometry. The fused hybridomas were inoculated into 384-well plates by the limited dilution method, and the supernatant was collected after ten days of culture to screen positive hybridoma clones by flow cytometry. After co-incubating the supernatant with UBER CLDNT8.2 TCF cells (20,000 cells/well) at 4° C. for 45 minutes, the plate was washed. Alexa Fluor®-488-goat anti-mouse IgG (ThermoFisher® Catalog No. A28175) was used as the secondary antibody for flow cytometry detection, and clones with an average fluorescence intensity of above 100,000 were screened for amplification, and the saturated supernatant was collected for confirmation screening.

3 batches of hybridomas were cloned by using the limited dilution method in 10 384-well plates per batch. After primary screening, 341 (MFI>100,000), 336 (MFI>75,000 or MFI>80,000) and 89 (MFI>90,000) hybridoma clones that positively bound to the mouse tumor cell line expressing CLDN18.2-TCF, were obtained from three batches of hybridomas, respectively.

2) Confirmation screening: the supernatant expression products of the positive clones screened in the previous step were incubated with HEK293-hCLDN18.2 cells, HEK293-hCLDN18.1 cells and HEK293 wild-type cells, respectively (20,000 cells/well, 4° C., 45 minutes). Clones positive for binding to HEK293-hCLDN18.2 cells but negative for binding to HEK293-hCLDN18.1 cells and HEK293 wild-type cells were screened by flow cytometry using Alexa Fluor®-488-goat anti-mouse IgG (ThermoFisher© Cat. No. A28175) as secondary antibody for amplification, and the saturated supernatant was collected for validation screening.

Figure 5:
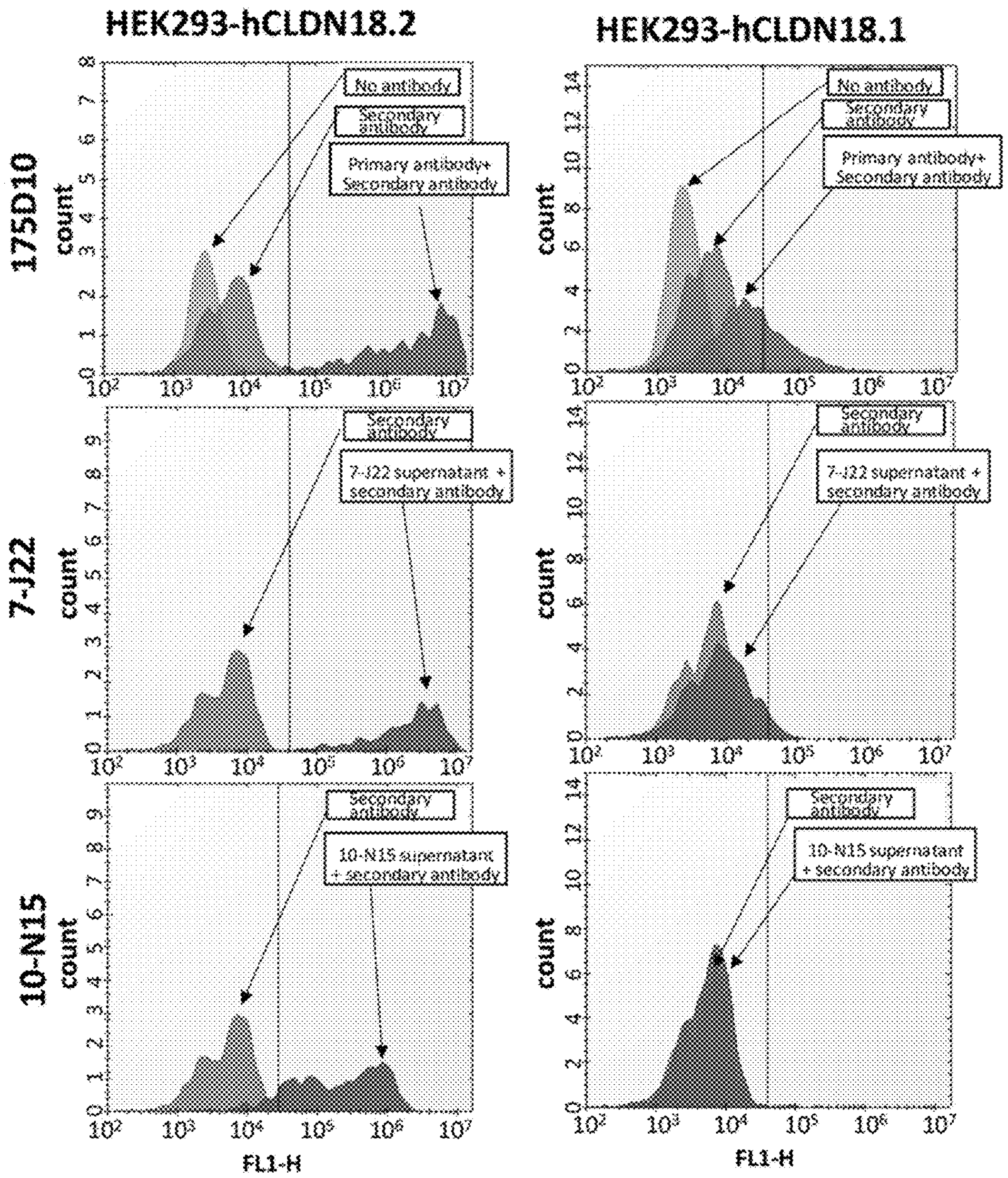
FIG. 5. Binding of the supernatant of positive hybridoma clones to HEK293-hCLDN18.2 cells and HEK293-hCLDN18.1 cells in confirmation screening.

After confirmation screening, 165 (HEK293-hCLDN18.2 MFI>200,000, HEK293-hCLDN18.1 MFI<100,000), 120 (HEK293-hCLDN18.2 MFI>50,000, HEK293-hCLDN18.1 MFI<40,000) and 21 (HEK293-hCLDN18.2 MFI>70,000, HEK293-hCLDN18.1 MFI<30,000) clones that can specifically bind to HEK293-hCLDN18.2 cells strongly but bind to HEK293-hCLDN18.1 cells weakly and does not bind to HEK293 wild-type cells, were obtained from three batches of hybridomas, respectively. FACS analysis of some positive clones was shown in FIG. 5.

Figure 6:
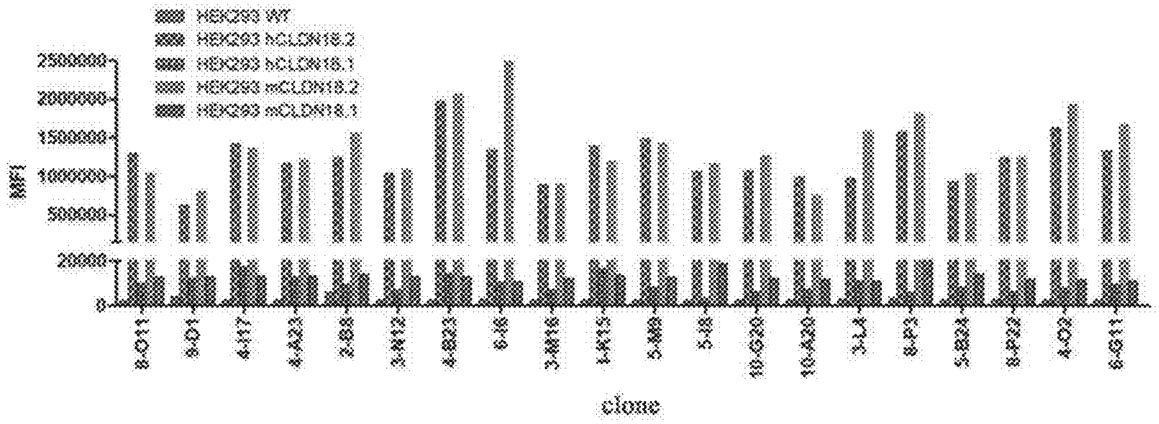
FIG. 6. Flow cytometry analysis of the supernatant of some positive hybridoma clones on 5 cell lines in validation screening.

3) Verification screening: the supernatant expression products of 306 (165+120+21) positive hybridomas obtained in the confirmation screening of three batches of hybridomas were incubated with HEK293-hCLDN18.2 cells, HEK293-hCLDN18.1 cells, HEK293-mCLDN18.2 cells, HEK293-mCLDN18.1 cells, and HEK293 wild-type cells (20,000 cells/well, 4° C., 45 minutes), and Alexa Fluor®-488-goat anti-mouse IgG (ThermoFisher® Cat. No. A28175) was used as a secondary antibody for analysis by flow cytometry. The flow cytometry analysis results of some clones on the 5 cell lines were shown in FIG. 6, showing that the mean fluorescence intensity (MFI) of positive clones in HEK293-hCLDN18.2 cells and HEK293-mCLDN18.2 cells exceeds 500,000, while the mean fluorescence intensity in HEK293-hCLDN18.1 cells, HEK293-mCLDN18.1 cells and HEK293 wild-type cell lines was all below 50,000, and the mean fluorescence intensity (MFI) of most clones (16/22) in HEK293-hCLDN18.2 cells and HEK293-mCLDN18.2 cells exceeds that in HEK293-hCLDN18.1 cells and HEK293-mCLDN18.1 cells 50 times.

4) Antibody typing: because different subtypes of IgG molecules also had different abilities to mediate ADCC effects. The antibodies of the expression products in the supernatant derived from 306 (165+120+21) positive hybridomas obtained in the three batches of hybridoma confirmation screening were subjected to mouse antibody subtyping using a mouse antibody subtype detection kit prior to antibody-dependent cell killing assay. Most of the 306 clones belong to mouse IgG2a, IgG2b or IgG3 with ADCC function, and only a few (26/306) were IgG1 subtype without ADCC function (corresponding to human antibody IgG4 subtype). Some clones were mixed subtypes, possibly because the hybridoma clones were not monoclonal. The light chains were all mouse kappa isoforms.

5) ADCC effect detection

Figure 7:
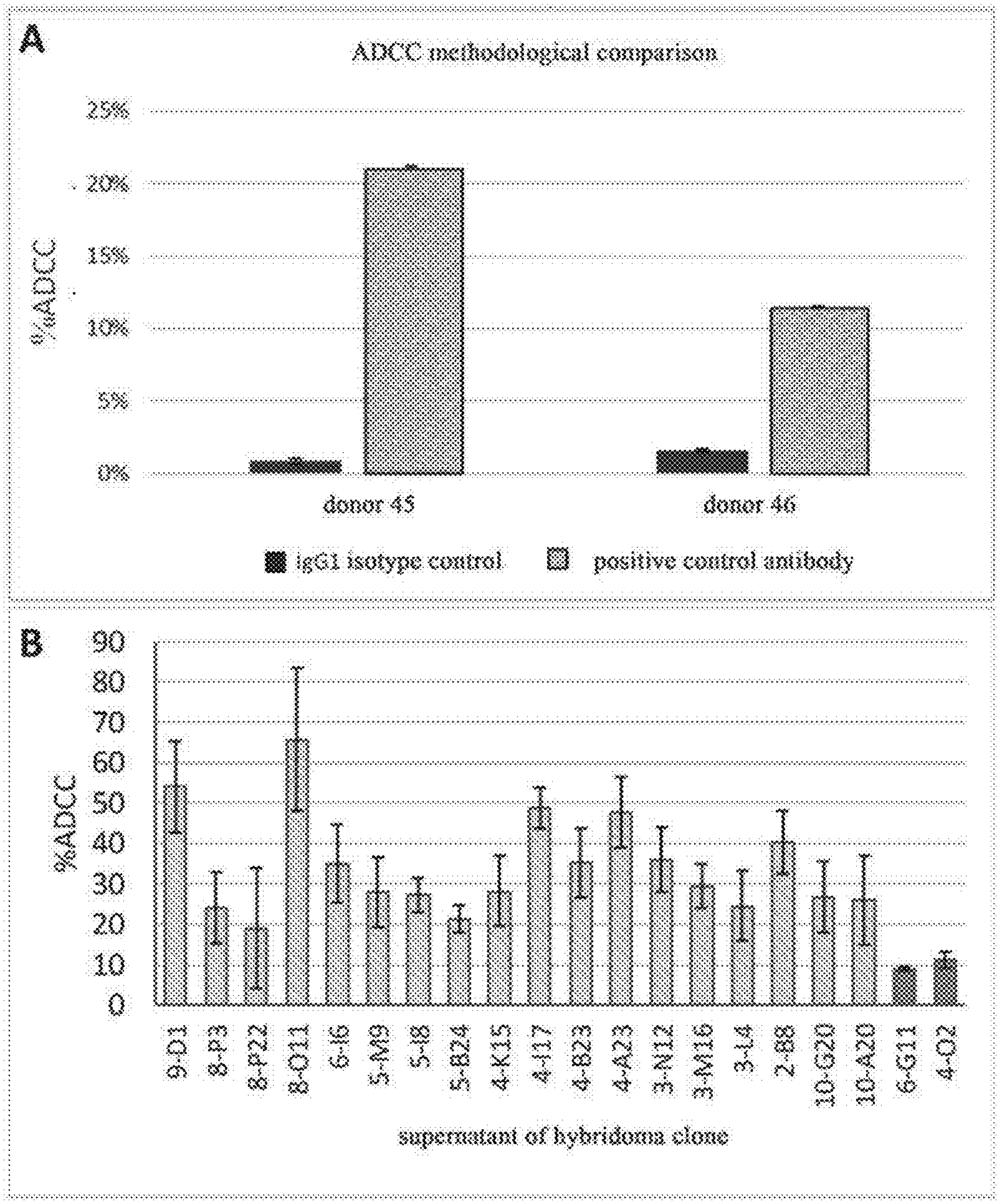
FIG. 7. ADCC effect of the supernatant of some positive hybridoma clones.

Taking into account the aforementioned confirmation screening, verification screening and antibody typing results, the saturated supernatants of 128 positive clones were selected for antibody-dependent cytotoxicity function detection. The effector cells were human peripheral blood mononuclear cells (PBMCs), which were derived from two donors (Nos. 45 and 46). Blood was drawn from the donors the day before the experiment. The collected blood was stored at room temperature, and the PBMCs were freshly isolated through the Ficoll gradient. The target cells were HEK293 cells expressing CLDN18.2 (HEK293-hCLDN18.2). The hybridoma expression products were uniformly diluted 4-fold. Freshly obtained PBMCs and target cells were incubated with each sample for 4 hours at an effect-to-target ratio of 25:1. ADCC effect of the antibody was characterized by measuring lactate dehydrogenase (LDH) associated with cytotoxicity. The absorbance value detected when the target cells were lysed spontaneously was defined as 0%, and the absorbance value detected when the target cells were completely lysed was defined as 100%, and the ADCC effect was characterized by the relative percentage activity of each test sample. The ADCC effect results of some clones were shown in FIG. 7. The ADCC killing effect of the clone supernatant was higher than 20% on average, the ADCC effect of some clones (9D-1, 8-O11) was higher than 50%, and the ADCC effect was less than 10% for mouse IgG1 subtypes 6-G11 and 4-02.

Example 4 Screening of Hybridomas with Positive Immunohistochemical Staining for hCLDN18.2 on PPFE Tissue Sections In the process of companion diagnosis, pathological detection of paraffin-embedded (FFPE) histological sections after biopsy of the patient's tumor tissue was a common procedure. Tumor associated antigen (TAA) loses its natural structure in the process of histological sectioning, and even if antigen retrieval was performed, the antigen can only restore part of the conformational structure to a certain extent, or only expose certain linear peptides. The supernatant of the above-mentioned preferred 128 positive hybridoma clones had the ability to specifically bind to the native CLDN18.2 conformation on the cell surface and ADCC function, but as a companion diagnostic antibody, IHC screening for antigen-specific binding must be performed on FFPE tissue sections. In this example, binding of the supernatant of 128 positive hybridoma on cell block paraffin-embedded (FFPE) tissue sections of 3 engineered cell lines (HEK293-hCLDN18.2 cells, HEK293-hCLDN18.1 cells, and HEK293 wild-type cells) was detected by immunohistology chemistry (IHC) method of PPFE tissue sections.

First, IHC staining was performed on FFPE tissue sections of HEK293 cell blocks stably expressing CLDN18, including culturing HEK293-hCLDN18.2 cells, HEK293-hCLDN18.1 cells and HEK293 wild-type cells, collecting cells, centrifuging to form cell blocks, then performing dehydration, clearing, and paraffin-embedding steps followed by FFPE tissue sectioning and IHC staining. The supernatant of hybridoma clones that can be positively stained on HEK293-hCLDN18.2 cell block FFPE tissue sections and negatively stained on HEK293-hCLDN18.1 cells and HEK293 wild-type cell block FFPE tissue sections was screened. Then, the obtained positive hybridoma supernatant was verified by IHC staining on FFPE tissue sections of human gastric cancer tissue. Finally, IHC staining was performed with the verified IHC-positive hybridoma supernatant on human normal stomach and gastric cancer FFPE tissue micro-array (TMA). The final IHC-positive colonies were determined according to the IHC staining intensity and staining ratio.

The IHC method of hybridoma clones for cell block FFPE tissue sections, gastric cancer FFPE tissue sections, and normal stomach and gastric cancer FFPE tissue micro-array (TMA) includes the following steps: 1) slide heating for deparaffinization: 60° C., 30 minutes; 2) deparaffinizing: immersion in three stages (I, II, III) of xylene, 5 minutes per stage; 3) hydration: immersion in gradient ethanol 100%×2 times, 95%×1 time, 75%×1 time, 3 minutes each time, and immersion in distilled water for 5 minutes; 4) antigen retrieval: the antigen retrieval solution (Tris-EDTA, pH=9.0) was put in a water bath at 100° C., and the FFPE tissue sections were put in the antigen retrieval solution, incubated for 30 minutes, cooled at room temperature for 30 minutes, and washed 3 times with PBS buffer for 5 minutes each time; 5) blocking: incubated in 3% H202-PBS for 10 minutes at room temperature in the dark, washed 3 times with PBS, then incubated in 5% BSA (PBS-BSA) for 60 minutes at room temperature, and washed 3 times with PBS buffer; 6) primary antibody incubation: commercial rabbit anti-CLDN18.2 positive antibody (EPR19202, Abcam®, Cat. No. ab222512) diluted 1:100, or mouse hybridoma supernatant, incubated overnight at 4° C.; 7) secondary antibody incubation: HRP-conjugated goat anti-rabbit (Abcam®, catalog number ab6721, 1:1000 dilution) and HRP-conjugated goat anti-mouse secondary antibody (ThermoFisher®, catalog number 62-6520, 1:2000 dilution); 8) staining: staining with diaminobenzidine (DAB) for 3 minutes; 9) counterstaining with hematoxylin for 1 minute, differentiation with 0.5% HCl-75% ethanol for several seconds, and bluing with running water for 20 minutes; 10) dehydration and clearing: dehydration with 70% ethanol, 80% ethanol, 95% ethanol, anhydrous ethanol I and anhydrous ethanol for 2 minutes each; clearing with Xylene I and Xylene II for 5 minutes each; 11) mounting: mounting with a neutral mounting medium.

Figure 8:
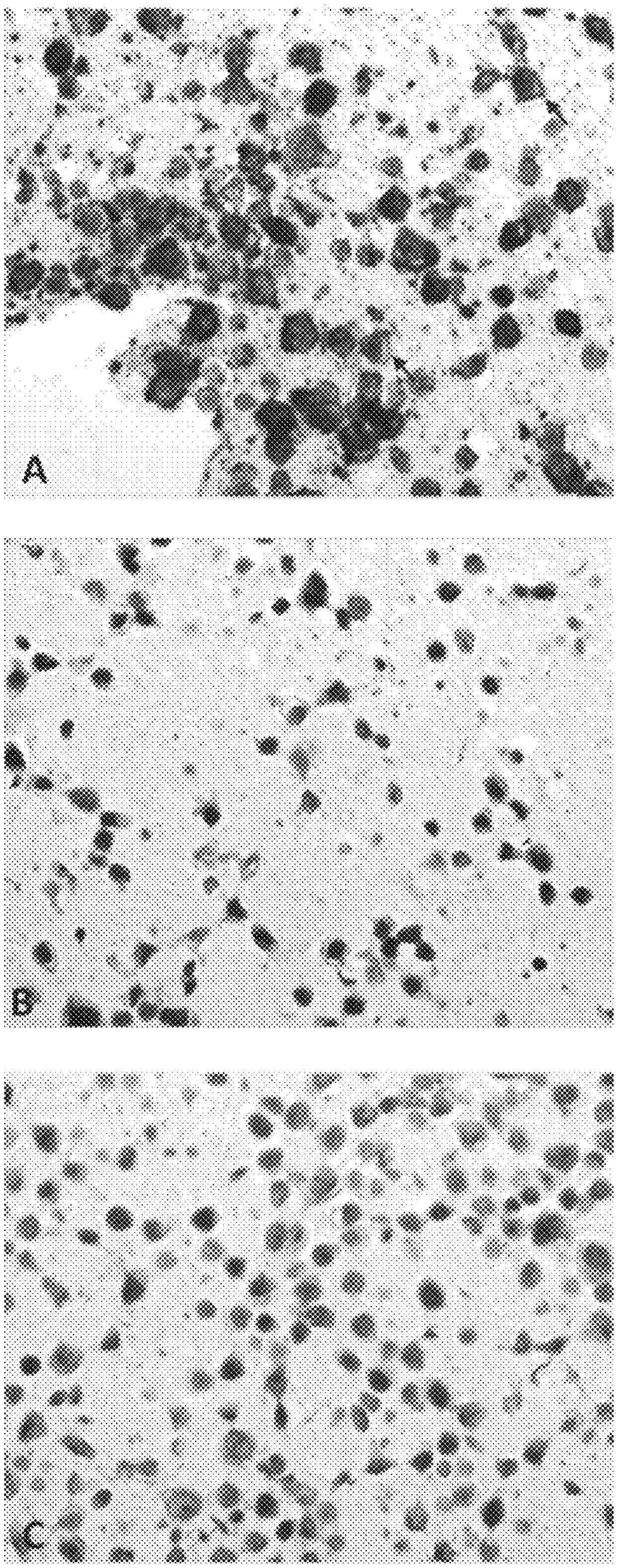
FIG. 8. IHC staining of the positive control antibody on paraffin-embedded (FFPE) tissue sections of the HEK293-hCLDN18.2 (A), HEK293-hCLDN18.1 (B) and HEK293-WT (C) cell blocks.

FIG. 8 showed the IHC staining results of the positive control commercial antibody EPR19202 on FFPE tissue sections of the HEK293 cell block, wherein the antibody can specifically stain FFPE tissue sections of the cell blocks of the HEK293-hCLDN18.2 stable cell line, and the positive staining was obvious at the location of the cell membrane (FIG. 8. A, indicated by the arrow), which was consistent with the conclusion that CLDN18.2 was a membrane protein (FIG. 8A). In contrast, the antibody showed no obvious staining on the FFPE tissue sections of the cell blocks of the stable HEK293-hCLDN18.1 cell line (FIG. 8B), and no obvious staining on the HEK293 wild cell line (FIG. 8C).

4 Hybridomas clones (5-I5, 5-I10, 5-G17 and 10-D3) were obtained by IHC staining of the supernatant of 120 hybridoma clones on FFPE tissue sections of cell blocks of the 3 cell lines (HEK293-hCLDN18.2 cells, HEK293-hCLDN18.1 cells and HEK293 wild-type cells). The supernatant of the clones shows positive IHC staining on FFPE tissue sections of the HEK293-hCLDN18.2 cell block, while showing no or weak staining on FFPE tissue sections of the HEK293-hCLDN18.1 and HEK293-WT cell blocks.

Figure 9:
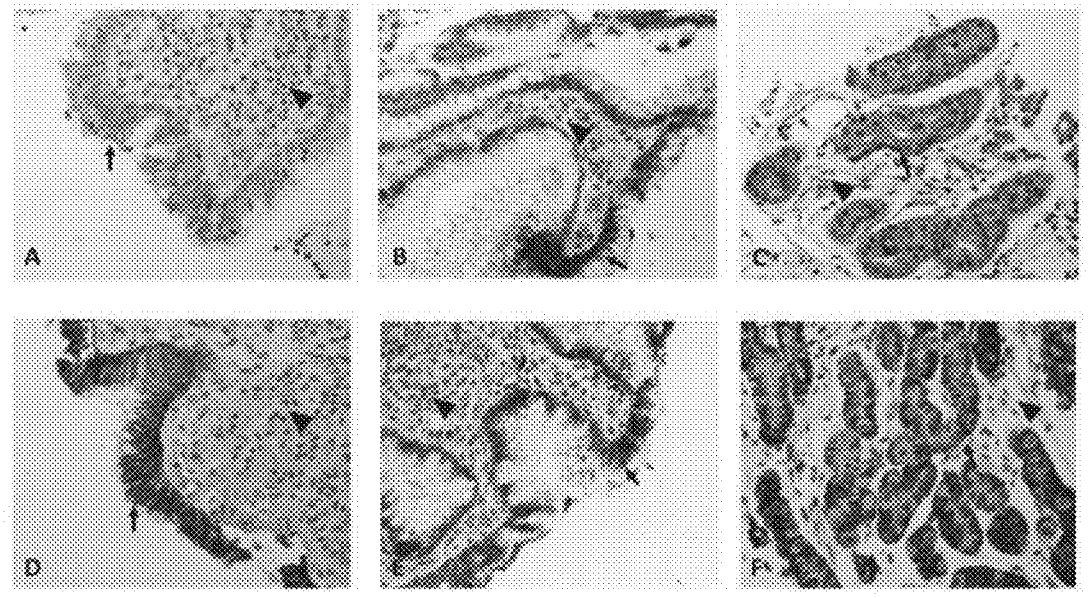
FIG. 9. IHC staining of the supernatant of 5-I5 hybridoma clone and the positive control antibody on paraffin-embedded (FFPE) tissue sections of the gastric cancer tissue.

The supernatant of 4 IHC-positive hybridoma clones screened using FFPE tissue sections of the HEK293-hCLDN18.2 cell block was verified by IHC staining on FFPE tissue sections derived from the human gastric cancer tissues, wherein the IHC staining results of the supernatant of hybridoma clone 5-I5 on FFPE tissue sections of 3 cases of human gastric cancer tissues were shown in FIG. 9 (A, B, C). The positive staining of the antibody only appears at the location of the glandular epithelial cells (indicated by the arrow), and there was no obvious positive chromogenic reaction or weak staining for stromal cells (indicated by triangular arrows). The positive staining positions and the positive staining tissue structure of 5-I5 on FFPE tissue sections of the 3 cases of gastric cancer tissues were relatively consistent with the IHC staining results of the positive control antibody (EPR19202) (FIGS. 9D, E and F).

As a companion diagnostic antibody, it was of great clinical significance to recognize a high proportion of patients with high expression of tumor-associated antigens for treatment. Because of the differences of cancer patients and the heterogeneity of tumor tissues of patients, the IHC staining results of different diagnostic antibodies against the same tumor-associated antigen were often different. We performed IHC staining of the supernatant with expression products of the 4 IHC positive candidate hybridomas and the mixture of the supernatant from the 4 (Cocktail) on the FFPE tissue microarray (TMA) chips (Biomax, ST807) of the human normal stomach and gastric cancer FFPE tissues. During antibody incubation, the incubation time of the supernatant of single hybridoma clone and positive control antibody was 30 minutes, and the incubation time of the supernatant mixture of 4 hybridomas was 120 minutes. Table 4 summarized the tissue sites and tissue types of membrane-positive staining and cytoplasmic-positive staining, and the corresponding positively stained clones. 5-I10, 5-G17, 5-I5, 10-D3 and the mixture of supernatant of the 4 clones showed cell membrane positive staining rates of 28.9%, 17.1%, 14.5%, 11.8% and 28.9% on all 76 tissue sites, respectively, and the cell membrane positive rate of the positive control antibody (EPR19202) was 23.7%. It was worth noting that almost all clone supernatant and positive antibodies were positively stained on normal gastric tissues (5-I10 87.5%, 5-G17 87.5%, 5-I5 100%, 10-D3 87.5%, Mix. Of 4 100%, EPR19202 100%), which was consistent with the specific expression of CLDN18.2 in normal gastric mucosa epithelial cells reported in the literature (Sahin. U. et al, Human Cancer Biology, 2008, 14(23), 7624-7634). Compared with the high positive rate staining of normal gastric tissue, the positive staining rate of each hybridoma supernatant on the gastric cancer tissue varies greatly, the cell membrane positive staining rates on gastric cancer tissues were 23.5% for 5-I10, 10% for 5-G17, 4.4% for 5-I5, 2.9% for 10-D3 and 22% for the mixture of supernatant of the 4 hybridomas (Mix. Of 4), which may be related to the high heterogeneity of the gastric cancer tissue. Among them, the supernatant of 5-I10 hybridoma clone had the highest positive staining rate in the gastric cancer tissue, reaching 23.5%, which was significantly higher than 14.7% of the positive control antibody EPR19202, and was substantially consistent with the positive rate of 16-23% reported by Zhu G. et al (Zhu G. et al, Sci Rep., 2019, 9: 8420-8431).

It should be particularly noted that the positive staining rates of 5-I10 and 5-G17 in the gastric cancer FFPE tissue was high, and the composite (5-I10+5-G17) positive rate of the two reached up to 26%. The gastric cancer FFPE tissue sites with positive staining sites substantially include the positive sites appeared on 5-I5 and 10-D3. Therefore, using recombinantly expressed and purified antibodies 5-I10 and 5-G17 in a certain proportion to form an antibody mixture for companion diagnosis can maximize the selection of gastric cancer patients with high CLDN18.2 expression, which was significant for guiding the clinical administration of drugs targeting CLDN18.2.

TABLE 4

| Position | Number | Diagnostic type | Mixture of 4 antibodies | 5-I10 | 5-G17 | 5-I5 | 10-D3 | EPR19202 |
|---|---|---|---|---|---|---|---|---|
| A6 | 6 | Gastric adenocarcinoma | M | M | M | M | M | M |
| H3 | 73 | Normal stomach tissue | M | M | M | M | M | M |
| H4 | 74 | Normal stomach tissue | M | M | M | M | M | M |
| H7 | 77 | Normal stomach tissue | M | M | M | M | M | M |
| H8 | 78 | Normal stomach tissue | M | M | M | M | M | M |
| H9 | 79 | Normal stomach tissue | M | M | M | M | M | M |
| H10 | 80 | Normal stomach tissue | M | M | M | M | C | M |
| F9 | 59 | Gastric adenocarcinoma | M | M | M | M | / | M |
| H6 | 76 | Normal stomach tissue | M | M | C | M | M | M |
| E2 | 42 | Gastric adenocarcinoma | M | M | M | C | / | / |
| F4 | 54 | Gastric adenocarcinoma | M | M | C | C | / | M |
| F1 | 51 | Gastric adenocarcinoma | M | M | C | C | / | C |
| B6 | 16 | Gastric adenocarcinoma | M | M | C | C | / | / |
| C1 | 21 | Gastric adenocarcinoma | M | M | / | / | / | M |
| B2 | 12 | Gastric adenocarcinoma | M | M | / | / | / | / |
| B3 | 13 | Gastric adenocarcinoma | M | M | / | / | / | / |
| C2 | 22 | Gastric adenocarcinoma | M | M | / | / | / | / |
| F10 | 60 | Gastric adenosquamous carcinoma | M | M | / | / | / | / |
| H5 | 75 | Normal stomach tissue | M | C | C | M | M | M |
| B7 | 17 | Gastric adenocarcinoma | M | C | M | C | / | / |
| C3 | 23 | Gastric adenocarcinoma | M | C | / | C | / | / |
| E4 | 44 | Gastric adenocarcinoma | M | / | / | / | / | / |
| C9 | 29 | Gastric adenocarcinoma | C | M | C | C | / | M |
| E1 | 41 | Gastric adenocarcinoma | C | M | / | C | / | / |
| C6 | 26 | Gastric adenocarcinoma | C | M | M | / | / | M |
| B10 | 20 | Gastric adenocarcinoma | C | M | / | / | / | / |
| A7 | 7 | Gastric adenocarcinoma | C | C | M | M | / | M |
| B8 | 18 | Gastric adenocarcinoma | C | C | M | C | / | / |
| A4 | 4 | Gastric adenocarcinoma | C | / | C | C | M | M |
| A5 | 5 | Gastric adenocarcinoma | C | C | C | C | C | M |
| D9 | 39 | Gastric adenocarcinoma | C | C | C | C | C | M |

TABLE 4-continued

| | | | | | | |
|---|---|---|---|---|---|---|
| Total cell membrane positive staining rate | 22/76 (28.9%) | 22/76 (28.9%) | 13/76 (17.1%) | 11/76 (14.5%) | 9/76 (11.8%) | 18/76 (23.7%) |

| Summary of tissue microarray IHC results | | Mixture of 4 antibodies | 5-I10 + 5-G17 mixture | 5-I10 | 5-G17 | EPR19202 |
|---|---|---|---|---|---|---|
| Cell membrane positive staining rate (%) | Normal stomach tissue | 8/8 (100%) | 7/8 (87.5%) | 7/8 (87.5%) | 7/8 (87.5%) | 8/8 (100%) |
| | Gastric cancer tissue | 15/68 (22%) | 18/68 (26%) | 16/68 (23.5%) | 7/68 (10%) | 10/68 (14.7%) |

Note:
1) the table counted the tissue sites with positive staining;
2) TMA had a total of 80 tissue sites, of which 4 tissue sites had poor tissue morphology and were excluded;
3) M indicated cell membrane positive staining, and C indicates cytoplasm positive staining, and / indicated negative staining.

Figure 10:
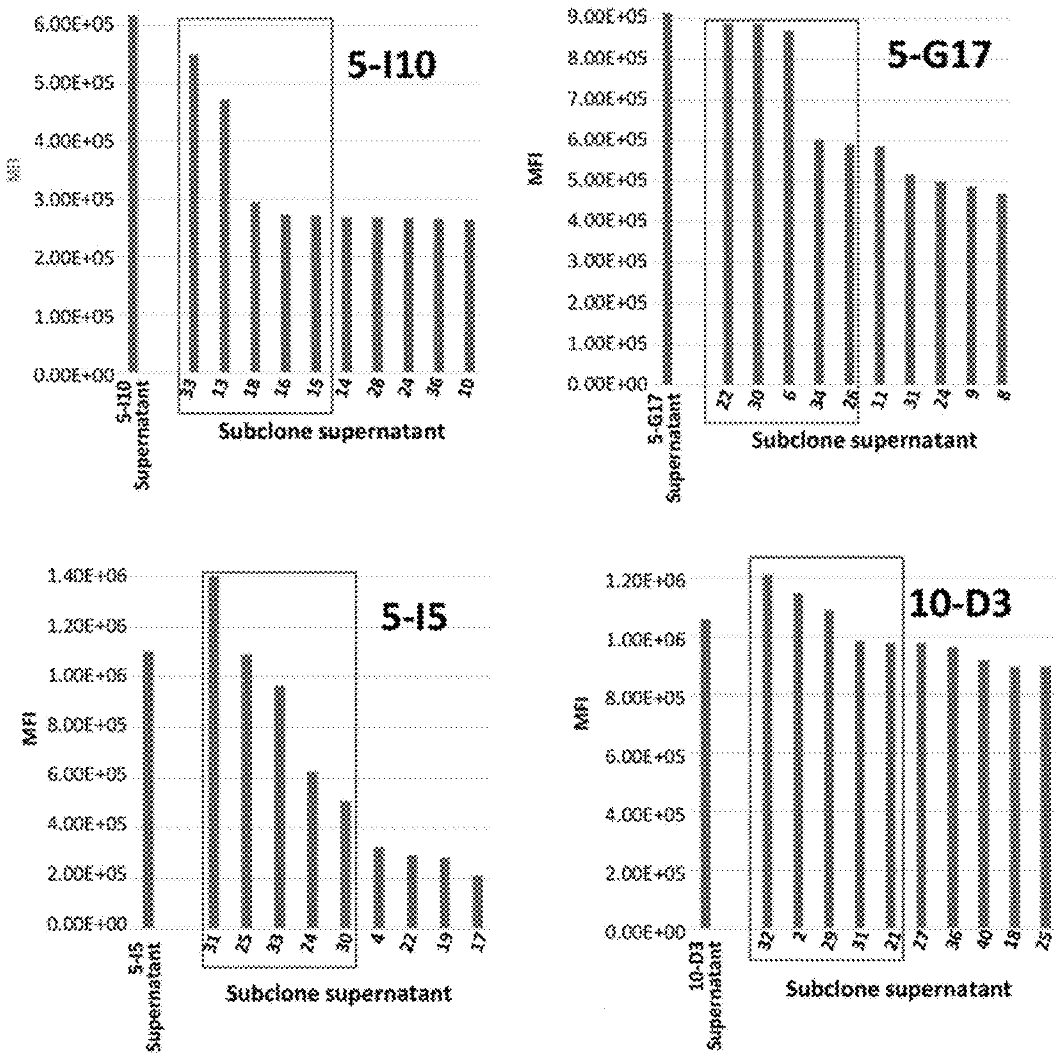
FIG. 10. Flow cytometry analysis of the hybridoma monoclonal supernatant on HEK293-hCLDN18.2 cells.

Example 5. Subcloning of Hybridoma Clones with hCLDN18.2 Positive Staining FFPE Tissue Sections and Sequencing for the Antibody Molecules In this example, the limited dilution method was used for subcloning of the 4 hybridoma clones (5-I10, 5-G17, 5-15 and 10-D3) with IHC-positive FFPE tissue sections and sequencing of the variable regions of the antibody molecules was performed. The thawed hybridoma clones were subjected to limited dilution and plated into 192-well plates at a density of 0.8 cell/well. Single clones were selected by microscopy, and the supernatant were collected after 14 days of culture. The specific binding of the subclone supernatant to HEK293-hCLDN18.2 cells was detected by flow cytometry analysis, and meanwhile the single clone was amplified and cultured. At the same time, single clones were amplified and cultured. The flow cytometric analysis method was as follows: after co-incubating the monoclonal supernatant with HEK293-CLDN18.2 cells (20,000 cells/well) at 4° C. for 45 minutes, the plate was washed, and Alexa Fluor®-488-goat anti-mouse IgG (ThermoFisher®, Catalog No. A28175) was used as a secondary antibody for flow cytometry detection. For each hybridoma, 10 (5-I5, 9) single clones were selected for amplification and cryopreservation, and the supernatant was collected for IHC staining verification on FFPE tissue sections. The flow cytometry analysis of HEK293-hCLDN18.2 cells using the monoclonal supernatant of 4 hybridomas was shown in FIG. 10, showing that the monoclonal supernatant maintains the specific binding to HEK293-hCLDN18.2 cells, and the binding intensity of part of the monoclonal supernatant to HEK293-hCLDN18.2 cells was comparable to that of the corresponding hybridoma supernatant (Parental supe.). The top 5 monoclonal supernatant (shown in blue box in FIG. 9) with the highest binding intensity to HEK293-hCLDN18.2 cells were selected from each hybridoma clone for IHC verification of FFPE tissue sections, and all monoclonal supernatant showed IHC positive staining. The 2 single clones with the highest IHC intensity on FFPE tissue sections were selected for each hybridoma (5-I5-31 and 5-I5-25, 10-D3-22 and 10-D3-21, 5-G17-30 and 5-G17-6, 5-I10-33 and 5-I10-18) for gene clone sequencing of the heavy and light chain variable regions.

The VH and VL DNA sequences of the hybridoma single clones were amplified using the RACE (rapid amplification of cDNA ends) method. RNA was extracted from amplified hybridoma monoclonal cells, which was reverse transcribed into cDNA and subjected to a 5'-RACE reaction using a combination of 5'-universal primers and 3'-H, L(κ) or L(λ) FR1 degenerate primers to perform PCR for the heavy chain or light chain V region, and the PCR-amplified fragments were ligated to a sequencing vector by the TOPO clone method for sequencing. Sequencing results showed that 5-I5-31 and 5-I5-25 had the same VH sequences, but different VL sequences, indicating that 5-I5-31 and 5-I5-25 were different single clones. Except for 5-I5, the two single clones sequenced for each of 10-D3, 5-G17 and 5-I10 had identical VH and VL, wherein the VH and VL DNA sequences of 5-I10 and 5-G17 were shown in Table 5, and the corresponding amino acid sequences were shown in Table 6, wherein the CDR regions in the light and heavy chains were divided according to the Chothia numbering system.

TABLE 5

| Antibody name | DNA sequences of the heavy chain V region |
|---|---|
| 5-I10 | GAGATCCAGCTGCAGCAGTCTGGAGCTGAGCTGGTGAAGCCTGGGGCTT<br>CAGTGAAGATATCCTGCAAGGCTCCTGGTTACTCATTCACTGACTACAATA<br>TGAACTGGGTGAAGCAGAGCCATGGAAAGAGCCTTGAGTGGATTGGAAA<br>TATTAATTCTTACTATGGTAGTACTAGCTACAATCAGAAGTTCAAGGGCAA<br>GGCCACATTGACTGTAGACAGATCTTCCAGCACAGCCTACATGCAGCTCA<br>ACAGCCTGACATCTGAGGACTCTGCAGTCTATTACTGTACAAACTTCGAC<br>AGGGGAAATTCGTTCCCTTACTGGGGCCACGGGACTCTGGTCACTGTCTC<br>TGCA(SEQ ID NO: 14) |
| 5-G17 | GAGGTGAAACTGGTGGAGTCTGGGGGAGGCTTAGTGAAGCCTGGAGGG<br>TCCCTGAAACTCTCCTGTGCAGCCTCTGGATTCACTATCAGTGACTACGG<br>AATGGCGTGGGTTCGACAGGCTCCAGGGAAGGGGCCTGAGTGGGTAGCA<br>TTCATTAGTAATTTGGCATATAGTATCCACTATGTAGACACTGTGACGGGC<br>CGATTCACCATCTCTAGAGAGAATGCCAAGAACACCCTGTACCTGGAAAT<br>GCGTAGTCTGAGGTCTGAGGACACAGCCATGTATTACTGTGCAAGAATGT<br>ACTATGGGAATGCTTTGGACTACTGGGGTCAAGGAACCTCAGTCACCGTC |

TABLE 5-continued

| | |
|---|---|
| | TCCTCA(SEQ ID NO: 15) |
| **Antibody name** | **DNA sequences of the light chain V region** |
| 5-I10 | GACATTGTGATGACACAGTCTCCATCCTCCCTGACTGTGACAGTAGGAGAGAAGGTCACTATGACCTGCAAGTCCAGTCAGAGTCTGTTAAACAGTGGAAATCAAAAGAACTATTTGACCTGGTACCAGCAGAAACCAGGGCAGTCTCCTAAACTGTTGATCTACTGGGCATCCACTAGGGAATCTGGGGTCCCTGAGCGCTTCACAGGCAGAGGATCTGGAACAGATTTCACTCTCACCATCAGCAGTGTGCAGGCTGAAGACCTGGCAGTTTATTACTGTCAGAATGGTTATAGTTATCCATTCACGTTCGGCTCGGGGACAAACTTGGAAATAAAA(SEQ ID NO: 16) |
| 5-G17 | GACATTGTGATGACACAGTCTCCATCCTCCCTGACTGTGACAACAGGAGAGAAGGTCACTATGAGTTGCAAGTCCAGTCAGAATCTGTTAAACAGTGGAAATCAAAAGAACTACTTGACCTGGTACCAGCAGAAACCAGGGCAGCCTCCTAAACTGTTGATCTACTGGGCATCCACTAGGGAATCTGGGGTCCCTGATCGCTTCACAGGCAGTGGATCTGGAACAGATTTCACTCTCACCATCAGCAGTGTGCAGGCTGAAGACCTGGCAGTTTATTACTGTCAGAATGATTATAGTTTTCCTCTCACGTTCGGTGCTGGGACCAAGCTGGAGCTGAAA(SEQ ID NO: 17) |

TABLE 6

| | Amino acid sequences of CDRs | | | | | | |
|---|---|---|---|---|---|---|---|
| Antibody name | FR1 | CDR1 | FR2 | CDR2 | FR3 | CDR3 | FR4 |
| | Heavy chain CDR (Chothia numbering) | | | | | | |
| 5-110 (heavy chain variable region: SEQ ID NO: 36) | EIQLQQSGAELVKPGASVKISCKAP(SEQ ID NO: 40) | GYSFTDY(SEQ ID NO: 18) | NMNWVKQSHGKSLEWIGNI(SEQ ID NO: 41) | NSYYGS (SEQ ID NO: 19) | TSYNQKFKGKATLTVDRSSSTAYMQLNSLTSEDSAVYYCTN(SEQ ID NO: 42) | FDRGNSFPY(SEQ ID NO: 20) | WGHGTLVTVSA (SEQ ID NO: 43) |
| 5-G17 (heavy chain variable region: SEQ ID NO: 38) | EVKLVESGGGLVKPGGSLKLSCAAS(SEQ ID NO: 44) | GFTISDY (SEQ ID NO: 21) | GMAWVRQAPGKGPEWVAFI(SEQ ID NO: 45) | SNLAYS (SEQ ID NO: 22) | IHYVDTVTGRFTISRENAKNTLYLEMRSLRSEDTAMYYCAR(SEQ ID NO: 46) | MYYGNALDY(SEQ ID NO: 23) | WGQGTSVTVSS (SEQ ID NO: 47) |
| | Light chain CDR sequences (Chothia numbering) | | | | | | |
| 5-110 (light chain variable region: SEQ ID NO: 37) | DIVMTQSPSSLTVTVGEKVTMTC(SEQ ID NO: 48) | KSSQSLLNSGNQKNYLT(SEQ ID NO: 24) | WYQQKPGQSPKLLIY(SEQ ID NO: 49) | WASTRES (SEQ ID NO: 25) | GVPERFTGRGSGTDFTLTISSVQAEDLAVYYC(SEQ ID NO: 50) | QNGYSYPFT(SEQ ID NO: 26) | FGSGTNLEIK (SEQ ID NO: 51) |
| 5-G17 (light chain variable region: SEQ ID NO: 39) | DIVMTQSPSSLTVTTGEKVTMSC(SEQ ID NO: 52) | KSSQNLLNSGNQKNYLT (SEQ ID NO: 27) | WYQQKPGQPPKLLIY(SEQ ID NO: 53) | WASTRES (SEQ ID NO: 28) | GVPDRFTGSGSGTDFTLTISSVQAEDLAVYYC(SEQ ID NO: 54) | QNDYSFPLT(SEQ ID NO: 29) | FGAGTKLELK(SEQ ID NO: 55) |

Example 6. Expression of Recombinant Mouse Monoclonal Antibody

The heavy and light chain V regions of 5-I10 and 5-G17 were fused with mouse IgG2a-type heavy chain constant regions (Table 7, Mouse IGHC2A, SEQ ID NO:30) and mouse kappa-type light chain constant regions (Table 7, Mouse IGKC, SEQ ID NO:31), respectively, and a signal peptide was added to the N-terminal of the heavy and light chain sequences, respectively. The mouse heavy chain full-length genes (SEQ ID NOs: 32, 33) and light chain full-length genes (SEQ ID NOs: 34, 35) of 5-I10 and 5-G17 were synthesized and cloned into expression vectors, and verified by sequencing (Genewiz Biotechnology Co., Ltd., Suzhou). The constructed expression plasmid of each candidate molecule was amplified and extracted, verified by agarose gel electrophoresis, and used as a transfection material.

Figure 11:
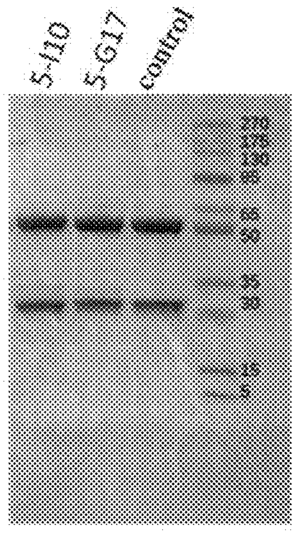
FIG. 11. Reduced SDS-PAGE electrophoresis of the purified recombinant mouse monoclonal antibodies 5-I10 and 5-G17.

HEK293 cells were inoculated into shake flasks for suspension seed culture using serum-free and chemically defined media. One day before transfection, the amplified HEK293 cells were inoculated into new shake flasks and replaced with fresh medium. The heavy chain and light chain expression plasmids of 5-I10 and 5-G17 were co-transfected into HEK293 cells, cultured in shake flasks until the cell viability decreases, and the supernatant was collected for product purification. First, most of the cell debris and insoluble particles were removed by centrifugation and filtration of the supernatant, and then the feed liquid was loaded onto the Protein A column, where the antibody molecules bind to Protein A on the filler. Most impurities were removed after an equilibration step, the antibody proteins were eluted using a low pH eluent to and the fractions were collected. pH was adjusted and exchanged to a formulation buffer by ultrafiltration. Finally, the OD280 was determined to calculate the protein concentration. As shown in FIG. 11, the electropherograms of monoclonal antibodies 5-I10 and 5-G17 on reducing SDS-PAGE showed that the positions of the heavy and light chains were consistent with the positions of the positive control IgG heavy and light chains, and the molecular weights were as expected. There was no obvious impurity band, and the protein purity was >95%.

TABLE 7

| | |
|---|---|
| Mouse IGKC | RADAAPTVSIFPPSSEQLTSGGASVVCFLNNFYPKDINVKWKIDGSERQNGV LNSWTDQDSKDSTYSMSSTLTLTKDEYERHNSYTCEATHKTSTSPIVKSFNR NEC(SEQ ID NO: 30) |
| Mouse IGHC2A | AKTTAPSVYPLAPVCGDTTGSSVTLGCLVKGYFPEPVTLTWNSGSLSSGVHT FPAVLQSDLYTLSSSVTVTSSTWPSQSITCNVAHPASSTKVDKKIEPRGPTIKP CPPCKCPAPNLLGGPSVFIFPPKIKDVLMISLSPMVTCVVVDVSEDDPDVQIS WFVNNVEVLTAQTQTHREDYNSTLRVVSALPIQHQDWMSGKEFKCKVNN KALPAPIERTISKPKGSVRAPQVYVLPPPEEEMTKKQVTLTCMVTDFMPEDI YVEWTNNGKTELNYKNTEPVLDSDGSYFMYSKLRVEKKNWVERNSYSCS VVHEGLHNHHTTKSFSRTPG(SEQ ID NO: 31) |

Figure 12:
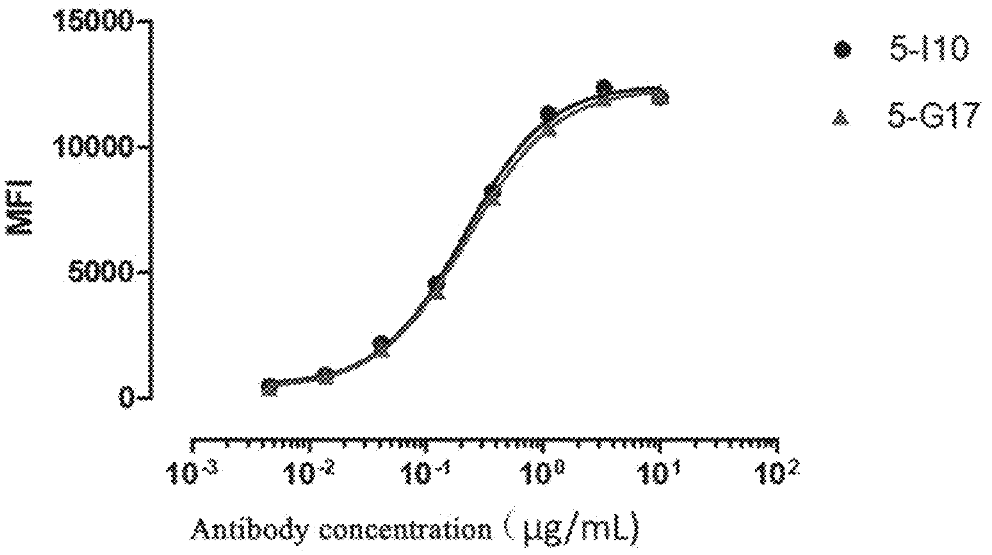
FIG. 12. Flow cytometric analysis of the purified recombinant monoclonal antibodies 5-I10 and 5-G17 in HEK293-hCLDN18.2.

Example 7. HEK293-hCLDN18.2 Binding Activity of the Recombinant Mouse Monoclonal Antibody The binding of purified monoclonal antibodies 5-I10 and 5-G17 to HEK293-hCLDN18.2 was verified by flow cytometry. HEK293-hCLDN18.2 was plated in a 96-well U-shaped plate ($1.5\times10^5$ cells/well), and the plate was washed once with PBS buffer containing 1% FBS. Purified monoclonal antibodies 5-I10 and 5-G17 were diluted with PBS (1% FBS) respectively, and a 3-fold gradient dilution was performed starting from the concentration of 10 μg/mL to obtain a total of 8 concentration points, they were then added to a 96-well U-plate at 100 μL/well and incubated at 4° C. for 1 hour. Washing once with PBS (1% FBS), and 100 μL/well of Alexa Fluor®488-labeled goat anti-mouse secondary antibody (eBioscience™, A11001) 1:1000 diluted was added and incubated at 4° C. for 1 hour. After washing twice with PBS (1% FBS), the cells were resuspended in 200 μL PBS (1% FBS) and detected by FACS. FIG. 12 showed the binding curves of purified monoclonal antibodies 5-I10 and 5-G17 to HEK293-hCLDN18.2, both antibodies can specifically bind to HEK293-hCLDN18.2 in a dose-dependent manner, with comparable binding abilities.

Figure 13:
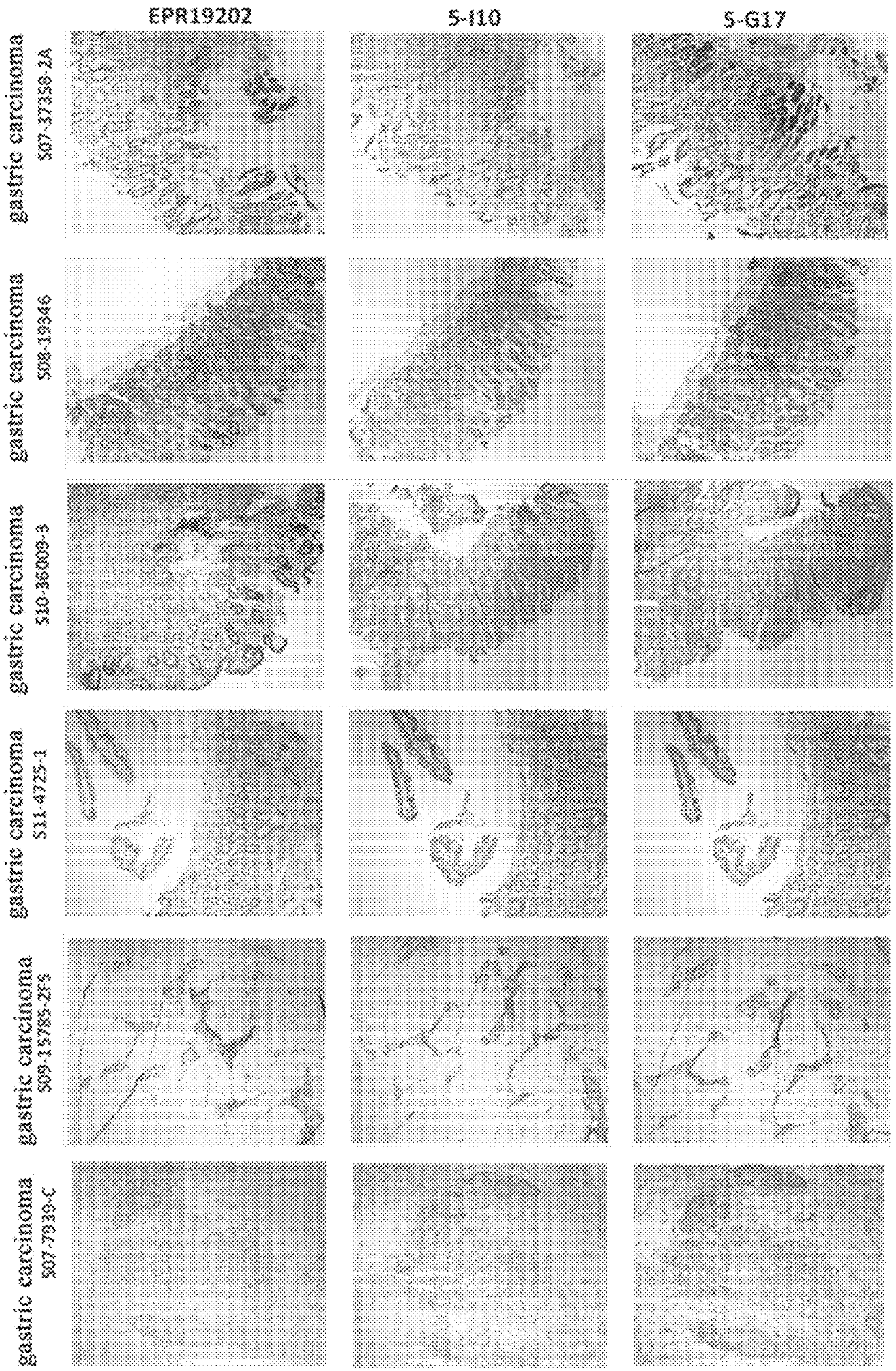
FIG. 13. Positive staining of the recombinant purified mouse monoclonal antibodies 5-I10 and 5-G17 on gastric cancer FFPE tissue sections.

Example 8. Positive Staining of the Recombinant Mouse Monoclonal Antibody on Gastric Cancer FFPE Tissue Sections The CLDN18.2 IHC positive staining of purified monoclonal antibodies 5-I10 and 5-G17 was verified on 6 cases of gastric cancer FFPE tissue sections, and EPR19202 was used as a positive control. The IHC staining procedure was the same as described in Example 4, wherein the working concentration of the positive control antibody EPR19202 in the primary antibody incubation step was 1:100 dilution, and the working concentration of purified antibodies 5-I10 and 5-G17 was 5 μg/mL. The staining results were shown in FIG. 13. The recombinant and purified mouse IgG2a type 5-I10 and 5-G17 monoclonal antibodies can be positively stained on several cases of gastric cancer FFPE tissue sections. The positive staining rates of 5-G17 and 5-I10 reached 83.3% (5/6) and 66.7% (4/6), respectively, which were significantly higher than 50% (3/6), which was that of the positive control antibody EPR19202. On tissues S07-37358-2A, S08-19346 and S10-36009-3, gastric cancer cells form a relatively obvious gastric gland epithelial structure, and 5-I10, 5-G17 and the positive control antibody EPR19202 all showed strong glandular epithelium-specific staining, but no staining on stromal cells. Gastric cancer cells form a gland-like structure on the S11-4725-1 tissue, but it was significantly different from the glandular structure on the aforementioned sections; the positive control SPR19202 had no obvious IHC staining, while 5-I10 and 5-G17 had strong positive staining, which was in diffuse type, and both glandular epithelium and stromal cells were stained. Tumor cells on S09-15785-2FS and S07-7939-C sections had no obvious glandular structure formed, and positive control SPR19202, 5-I10 and 5-G17 had no positive IHC staining on S09-15785-2FS. Only 5-G17 showed weak IHC positive staining on S07-7939-C.

The invention claimed is:

1. A CLDN18.2 monoclonal antibody comprising heavy chain CDRs and light chain CDRs, wherein the heavy chain CDRs comprise:

CDR1 having the sequence of SEQ ID NO:18, CDR2 having the sequence of SEQ ID NO:19, and CDR3 having the sequence of SEQ ID NO:20, and wherein the light chain CDRs comprise:

CDR1 having the sequence of SEQ ID NO:24, CDR2 having the sequence of SEQ ID NO:25, and CDR3 having the sequence of SEQ ID NO:26; or wherein the heavy chain CDRs comprise:

CDR1 having the sequence of SEQ ID NO:21, CDR2 having the sequence of SEQ ID NO:22, and CDR3 having the sequence of SEQ ID NO:23, and wherein the light chain CDRs comprise:

CDR1 having the sequence of SEQ ID NO:27, CDR2 having the sequence of SEQ ID NO:28, and CDR3 having the sequence of SEQ ID NO:29;

wherein the CDRs are numbered according to Chothia system.

2. The CLDN18.2 monoclonal antibody of claim 1, comprising the heavy chain variable region having the sequence of SEQ ID NO:36 and the light chain variable region having the sequence of SEQ ID NO:38.

3. The CLDN18.2 monoclonal antibody of claim 1, comprising a heavy chain variable region as shown in SEQ ID NO:37 and a light chain variable region as shown in SEQ ID NO: 39.

4. The CLDN18.2 monoclonal antibody of claim 1, which is a chimeric antibody or a humanized antibody.

5. The CLDN18.2 monoclonal antibody of claim 1, which is an IgG antibody.

6. The CLDN18.2 monoclonal antibody of claim 5, which is Fab, Fab'-SH, Fv, scFv or $(Fab')_2$.

7. The CLDN18.2 monoclonal antibody of claim 1, which is a multispecific antibody or a bispecific antibody.

8. The CLDN18.2 monoclonal antibody of claim 7, wherein the multispecific or bispecific antibody comprises a binding domain that binds to a second biomolecule, wherein the second biomolecule is a cell surface antigen.

9. The CLDN18.2 monoclonal antibody of claim 8, wherein the cell surface antigen is a tumor antigen.

10. The CLDN18.2 monoclonal antibody of claim 9, wherein the tumor antigen is selected from the group consisting of: CD3, CD20, FcRH5, HER2, LYPD1, LY6G6D, PMEL17, LY6E, CD19, CD33, CD22, CD79A, CD79B, EDAR, GFRA1, MRP4, RET, Steap1 and TenB2.

11. An immunoconjugate, comprising a therapeutic agent, an agonist of stimulator of interferon genes (STING) receptor, a cytokine, a radionuclide or an enzyme linked to the CLDN18.2 monoclonal antibody of claim 1.

12. The immunoconjugate of claim 11, wherein the therapeutic agent is a chemotherapeutic drug or a cytotoxic agent.

13. A fusion protein or polypeptide comprising the CLDN18.2 monoclonal antibody of claim 1 or an antigen-binding fragment thereof.

14. A pharmaceutical composition comprising the CLDN18.2 monoclonal antibody of claim 1.

15. A cancer detection reagent comprising the CLDN18.2 monoclonal antibody of claim 1 or an antigen-binding fragment thereof.

16. The cancer detection reagent of claim 15, wherein the CLDN18.2 monoclonal antibody or antigen-binding fragment thereof is chemically labeled.

17. The cancer detection reagent of claim 16, wherein the label is an enzymatic label, a fluorescent label, an isotopic label or a chemiluminescent label.

18. A cancer diagnosis kit comprising the cancer detection reagent of claim 15, wherein the cancer is a CLDN18.2-related cancer.

19. The kit of claim 18, wherein the cancer is a gastric cancer, a pancreatic cancer or an esophageal cancer.

* * * * *